United States Patent
Heindel et al.

(10) Patent No.: US 6,255,324 B1
(45) Date of Patent: Jul. 3, 2001

(54) AMINO-AND MERCURIO-SUBSTITUTED 4', 5'-DIHYDROPSORALENS AND THERAPEUTICAL USES THEREOF

(76) Inventors: Ned D. Heindel, 200 Hexenkopf Rd., Easton, PA (US) 18042-9570; Jeffrey D. Laskin, 69 Lakeside Dr. N., Piscataway, NJ (US) 08854; Diane E. Heck, 10 First St., Rumson, NJ (US) 07760; Robert D. Rapp, 1804 Elizabeth Ave., Laurel Dale, PA (US) 19605; Marilyn S. Whittemore, 2026 Widgeon Way Dr., Germantown, TN (US) 38138; Thomas E. McNeel, 3509 Amesbury, Memphis, TN (US) 38135; Ivan Jabin, Faculte des Sciences et Techniques, Universite du Havre, 25 rue Philippe Lebon, 76600 Le Havre (FR)

( * ) Notice: Subject to any disclaimer, the term of this patent is extended or adjusted under 35 U.S.C. 154(b) by 0 days.

(21) Appl. No.: 09/199,552

(22) Filed: Nov. 25, 1998

(51) Int. Cl.[7] .............. A61K 31/4709; A61K 31/37; C07D 493/04; C07D 405/14; A61P 35/00

(52) U.S. Cl. .............. 514/314; 514/232.8; 514/338; 514/455; 544/150; 546/152; 546/283.1; 549/209; 549/282; 549/387

(58) Field of Search ................ 549/209, 387, 549/282; 546/152, 283.1; 544/150; 514/314, 338, 455, 232.8

(56) References Cited

U.S. PATENT DOCUMENTS

| | | | |
|---|---|---|---|
| 4,124,598 | 11/1978 | Hearst et al. | 260/343.21 |
| 4,130,568 | 12/1978 | Confalone et al. | 260/343.21 |
| 4,196,281 | 4/1980 | Hearst et al. | 536/28 |
| 4,294,822 | 10/1981 | Kaufman | 424/59 |
| 4,950,770 | 8/1990 | Heindel et al. | 549/282 |
| 5,216,176 | 6/1993 | Heindel et al. | 549/280 |
| 5,356,929 | 10/1994 | Heindel et al. | 514/455 |
| 5,473,083 | 12/1995 | Heindel et al. | 549/280 |
| 5,625,079 | 4/1997 | Wollowitz et al. | 549/282 |
| 5,654,443 | 8/1997 | Wollowitz et al. | 549/282 |

FOREIGN PATENT DOCUMENTS

| | | |
|---|---|---|
| WO 90/08529 | 8/1990 | (WO). |
| WO 99/26476 | 6/1999 | (WO). |

OTHER PUBLICATIONS

Adams, R. et al., "The Structure of the Compounds Produced from Olefins and Mercury Salts: Mercurated Dihydrobenzofurans", *The Journal of the American Chemical Society*, 1922, pp. 1781–1792.

Bravo, P. et al., "Total Synthesis of Homochiral 3–Deoxy–3–Flouromuscarines", *Gazzetta Chimica Italiana*, 1990, pp. 275–276.

Cole, R.S., "Repair of DNA Containing Interstrand Crosslinks in *Escherichia coli*: Sequential Excision and Recombination", *Proc. Nat. Acad. Sci.*, 1973, pp. 1064–1068.

Corey, E.J. et al., "Total Synthesis of Picrotoxinin", *Journal of the American Chemical Society*, 1979, pp. 5841–5843.

Hearst, J., "Photochemistry of the Psoralens", *Chemical Research in Toxicology*, 1989, pp. 69–75.

(List continued on next page.)

Primary Examiner—Evelyn Mei Huang
(74) Attorney, Agent, or Firm—Morgan, Lewis & Bockius LLP

(57) ABSTRACT

5'-substituted, 4',5'-dihydropsoralen compounds (5) bearing tertiary amines (and salts thereof), quaternary ammonium moieties or organomercurial moieties are described.

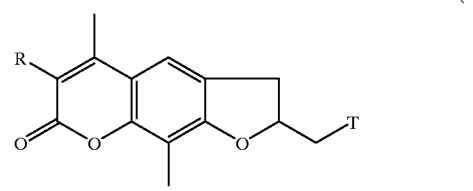

(5)

Also described are 2-substituted mercurimethyl-2-3-dihydro-benzofurans of forumla (7):

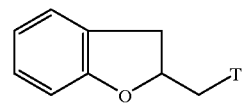

(7)

Also reported are versatile direct syntheses through a hitherto unknown compounds such as 3-R-4,8-dimethyl-4',5'-dihydro-5'-bromomethylpsoralen or a 3-R-4,8-dimethyl-4', 5'-dihydro-5'-iodomethylpsoralen to prepare a structurally diverse array of partially reduced psoralens and benzofurans. The presence of a permanent ammonium charge in these psoralens precludes membrane passage and the mono-unsaturation precludes the cross-linking of nuclear DNA, thereby minimizing the mutagenic/carcinogenic side effects long associated with psoralen-derived therapies. The presence of a mercury functionality provides a reactive cell-binding group on these psoralens with unique cytotoxicity without light activation and an enhancement of cytotoxicity activity upon light activation. The invention also relates to These partially reduced and quaternized psoralens, amino-substituted psoralens, and mercurio psoralens display impressive pharmacology against PAM 212 keratinocytes, a model cell line employed as a test system to indicate epidermal cytotoxicity and cancer. The compounds of the invention also have antimicrobicidal activity useful in pharmacologic agents for mammals (e.g. the treatment of tuberculosis) as well as in controlling the growth of microorganisms on substrates and in aqueous systems.

25 Claims, No Drawings

OTHER PUBLICATIONS

Heindel, N.D. et al., "Syntheses of Psoralen Analogues and Evaluation of Their Inhibition of Epidermal Growth Factor Binding", *Journal of Pharmaceutical Sciences*, 1991, pp. 686–689.

Isaacs, S.T. et al., "Synthesis and Characterization of New Psoralen Derivatives with Superior Photoreactivity with DNA and RNA", *Biochemistry*, 1977, pp. 1058–1064.

Kaufman, K.D. et al, "Synthetic Furocoumarins. I. A New Synthesis of Methyl–substituted Psoralenes and Isopsoralenes", *The Journal of Organic Chemistry*, 1961, pp. 117–121.

Kitano, K. et al., "Macrophage–Active Colony–Stimulating Factors Enhance Human Immunodeficiency Virus Type 1 Infection in Bone Marrow Stem Cells", *Blood : Journal American Society of Hematology*, 1991, pp. 1699–1705.

Laskin, J.D. et al., "A Possible Mechanism of Psoralen Phototoxicity not involving Direct Interaction with DNA", *Proc. Natl. Acad. Sci.*, 1985, pp. 6158–6162.

Laskin, J.D. et al., "Basis for Natural Variation in Sensitivity to 5–Fluorouracil in Mouse and Human Cells in Culture", *Cancer Research*, 1979, pp. 383–390.

Laskin, J.D. et al., "Psoralen Binding and Inhibition of Epidermal Growth Factor Binding By Psoralen/Ultraviolet Light (PUVA) in Human Epithelial Cells", *Biochemical Pharmacology*, 1991, pp. 125–132.

Laskin, J.D. et al., Selective Inactivation of Lymphocytes after Psoralen/Ultraviolet Light (PUVA) Treatment Without Affecting Systemic Immune Responses, *Journal of Leukocyte Biology*, 1993, pp. 138–144.

Mills, L. et al, "Mercurated 1–Methyl–1,2–Dihydro–Benzofurans", *The Journal of American Chemical Society*, 1923, pp. 1842–1854.

Morison, W.L. et al., "Consensus Workshop on the Toxic Effects of Long–Term PUVA Therapy", *Archives of Dermatology*, 1998, pp. 595–598.

Orita, K. et al., "Synthesis of 5–Iodobenzofurans and 6–Iodobenzopyrans via Direct Iodination with Mercury(II) Oxide–Iodine Reagent", *Synthesis*, 1997, pp. 23–25.

Rai, S. et al., "Dramatic Improvements in Viral Inactivation with Brominated Psoralens, Naphthalenes and Anthracenes", *Photochemistry and Photobiology*, 1993, pp. 59–65.

Reitz, A.B. et al., "Stereoselectivity of Electrophile–Promoted Cyclizations of $\gamma$–Hydroxyalkenes. An Investigation of Carbohydrate–Derived and Model Substrates", *J. Org. Chem.*, 1987, pp. 4191–4202.

Stern, R. et al., "Cutaneous Squamous–Cell Carcinoma in Patients Treated with PUVA", *The New England Journal of Medicine*, 1984, pp. 1156–1161.

Yurkow, E.J. et al., "Mechanism of Action of Psoralens: Isobologram Analysis Reveals that Ultraviolet Light Potentiation of Psoralen Action is not Additive But Synergistic", *Cancer Chemother Pharmocology*, 1991, pp. 315–319.

Adams, R. et al., *Organic Reactions*, 1949, vol. 5., pp. 200–207.

Beckwith, Athelstan L.J. et al., Iododediazoniation of Arenediazonium Salts Accompanied by Aryl Radical Ring Closure, *The Journal of Organic Chemicals*, 1987, vol. 52, pp. 1922–1930.

Meijs, G.F. et al., Formation of Functionalized Dihydrobenzofurans by Radical Cyclization, *The Journal of American Chemical Society*, 1986, vol. 108, pp. 5890–5893.

Wulff, et al., "Alkoxypsoralens, Novel Nonpeptide Blockers of Shaker–Type $K^+$ Channels: Synthesis and Photoreactivity, " *J. Med. Chem.*, 41, Nov. 1998, pp. 4542–4549.

Jabin, I. et al., "Synthetic Approaches to 3–Substituted–5'(N–pyridiniummethyl)–4',5'–dihydropsoralen", *Journal of Heterocyclic Chemistry*, 37, pp. 31–39 (2000).

Jabin, I. et al., "ACS National Meeting, Division of Organic Chemistry, 214th, Abstract 336", Sep. 1997.

Sastri et al., Proc.–Indian Acad. Sci. Sect. A, 37, pp. 681, 695, 1953.*

* cited by examiner

AMINO-AND MERCURIO-SUBSTITUTED 4', 5'-DIHYDROPSORALENS AND THERAPEUTICAL USES THEREOF

FEDERAL SUPPORT

This invention arose, at least in part, from research funded by NIH grants ES03647 and ES06897.

FIELD OF THE INVENTION

This invention relates to amino- and mercurio-substituted 4',5'-dihydropsoralens and 2-substituted mercurimethyl-2-3-dihydro-benzofurans and their use as phototherapeutics. Methods for preparing the amino- and mercurio-substituted 4',5'-dihydropsoralens and the 2-substituted mercurimethyl-2-3-dihydro-benzofurans via ring closure reactions and synthetic intermediates are also described.

BACKGROUND OF THE INVENTION

Linear fluorocoumarins, also known as psoralens, have been used in combination with ultraviolet light for centuries in cosmetics and for the treatment of proliferative skin diseases such as, for example, vitiligo, eczema, mycosis fungoides, and psoriasis. Terms such as photosensitization, photochemotherapy, photopheresis and PUVA (psoralens ultra violet A radiation) are commonly used to refer to such methods. Recently it was discovered that by modifying the administration of psoralen and ultraviolet light to an offending condition, psoralens can be used to treat cancer (e.g., T cell lymphoma), autoimmune diseases, and microbial infection.

The basic structure of psoralen, with the ring numbering structure used throughout the specification, is shown below:

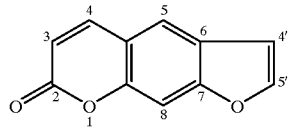

All psoralens contain two photo-activatable functions (absorbing in the UVA range)—an aryl-conjugated unsaturated pyrone (the coumarin portion) and an aryl-conjugated vinyl ether (the furan portion). All of the commercially available psoralens are highly lipophilic, non-nitrogenous, uncharged small molecules with minimal water solubility. Commercial psoralens are used in over-the-counter cosmetic creams, prescription pharmaceuticals, and as investigational candidates for many of the uses described above. The commercial psoralens in cosmetic/medical use include methoxsalen (also known as xanthotoxin, 8-methoxypsoralen or 8-MOP), trisoralen (also called 4,5', 8-trimethylpsoralen, TMP, or trioxsalen), and bergaptan (alternatively named 5-methoxypsoralen or 5-MOP).

The phototherapeutic action of psoralens has been discussed for example, by J. E. Hearst, "Photochemistry of the Psoralens," Chemical Research in Toxicology, 2, 69, 1989 and T. F. Anderson and J. J. Vorhees, Annual Reviews of Pharmacol. and Toxicol., vol. 10, p. 177, 1982. According to these articles, the highly lipophilic psoralens penetrate the target cell's membrane, intercalate into nuclear DNA, and photo crosslink the double helix through bis-cyclobutanes generated from the 3,4-double bond and the 4',5'-double bond [see numbering shown above] to double bonds in DNA's pyrimidine bases. Thus, because the crosslinked DNA is unable to uncoil and function as a template for new gene expression, the target cell is rendered non-viable.

A severe limitation to the acceptance of psoralen-based photochemotherapy or cosmetic skin pigment enhancement, however, is the risk of genetic mutations induced by DNA damage since the natural cellular level repair processes of bi-functional DNA-crosslinks are highly error-prone. Errors in cellular repair processes of true crosslinks translate to mutagenic/carcinogenic events and, in the clinical use of psoralens, represent a significant post-treatment risk of cancer. See, for example, R. S. Stern et al, "Cutaneous Squamous-cell Carcinoma in patients treated with PUVA," New England J. of Med., 1984, pp. 1156–116; R. S. Stern et al, "Malignant Melanoma in Patients Treated for Psoriasis with Methoxsalen and Ultraviolet A Radiation (PUVA)," New England Journal of Medicine, vol. 336, 1997, pp 1041–1045; and W. L. Morrison et al. "Consensus Workshop of the Toxic Effects of Long-Term PUVA Therapy," Arch. Dermatol., vol. 134, 1998, pp. 595–598.

The use of nonlinear furocoumarins (known as angelicins) for the treatment of psoriasis and other skin diseases is taught, for example by U.S. Pat. No. 4,312,883. According to the patent, nonlinear furocoumarins are an effective photochemotherapeutic compounds that does not have the risks associated with psoralens. Nonlinear furocoumarins, however, are limited by their structural geometry, forming only non-crosslinked mono-adducts which have diminished mutagenic behavior. See, for example, R. S. Cole, "Repair of DNA Containing Interstrand Crosslinks in E. Coli," Proc. Nat. Acad. Sci., volume 70, 1973, p. 1064. Further, lipophilic linear psoralens, capable of forming only monoadducts, can be phototoxic to malignant cells. See J. VanDongen, N. D. Heindel et al., "Synthesis of Psoralen Analogs and Evaluation of their Inhibition of Epidermal Growth Factor Binding," J. Pharm. Sci., volume 80, No. 7, July 1991, pp. 686–689.

Despite such risks, an alternative mechanism exists, not involving DNA, by which psoralens can act as phototoxins to a cell. A 22 kDa receptor protein present on psoralen-sensitive cells has been identified as a binding site for photo-activated psoralens. Binding a psoralen to this non-nuclear receptor follows UVA light activation of the psoralen and blocks subsequent binding of epidermal growth factor (EGF) to that receptor. The existence of this non-nuclear target has been described in J. D. Laskin et al., "A Possible Mechanism of Psoralen Phototoxicity Not Involving Direct Interaction with DNA," Proc. Nat. Acad. Sci., vol. 82, pp. 6158–6161, September 1985.

U.S. Pat. Nos. 5,473,083 and 5,216,176 report that reduced and quaternized psoralens are valuable photo-activated therapeutics. Although promising as therapeutics, these dihydro quaternary compounds have often been extremely difficult to synthesize. Furthermore, the reported method of synthesis does not permit access to 5'-(N-pyridiniummethyl) psoralens. 5'-N-pyridiniummethyl) psoralens had been found (in the related fully unsaturated psoralens) to be potent members (active at the lowest concentration levels) of the fully unsaturated psoralens. See Table 1, U.S. Pat. No. 5,216,176. Thus, a need exists for a new synthetic route suitable for 4',5'-dihydro psoralens bearing pyridinium, alkyl amino, alkyl ammonium, or other nitrogen-heterocyclic groups at the 5'-methyl locus.

U.S. Pat. No. 5,473,083 reports the synthesis of 5'-bromomethyl and 5'-quaternary ammonium psoralens (2, with T=Br or $R_3N+$). But, as Scheme 1 below shows, hydrogenolysis of the pendant leaving group-to-carbon bond, not hydrogenation of the 4',5'-double bond, is the dominant outcome when catalytic hydrogenation or exchange hydrogenation are attempted. This unfortunate consequence leads to the recovery of the parent psoralen.

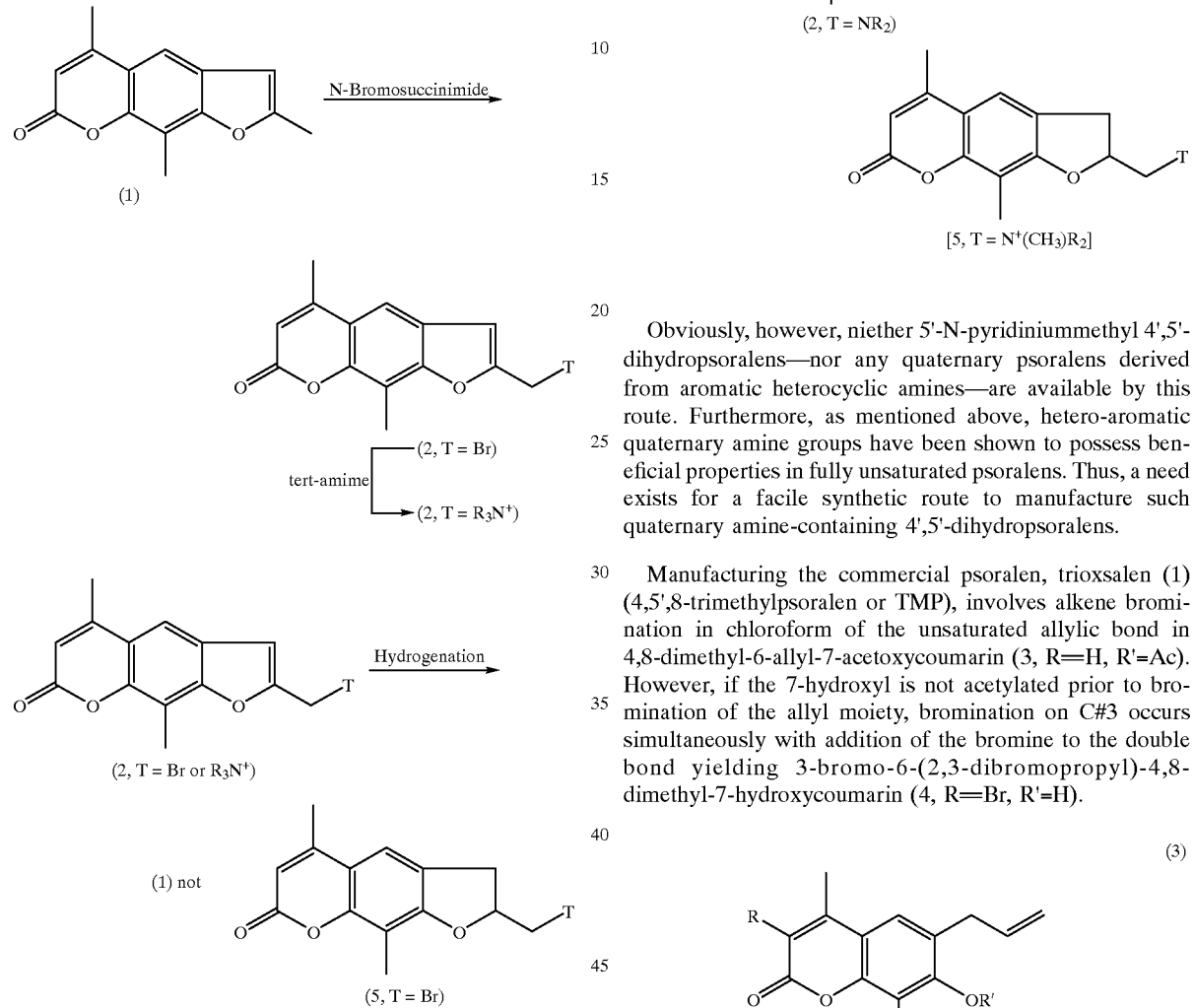

U.S. Pat. No. 5,356,929 discloses the preparation of less labile (to hydrogenolysis) tertiary aminomethylpsoralen. Reduction and subsequent methylation can produce methylated quaternary compounds in low overall yields (35–40%). This is shown in Scheme 2.

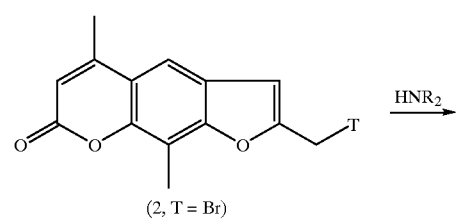

Obviously, however, niether 5'-N-pyridiniummethyl 4',5'-dihydropsoralens—nor any quaternary psoralens derived from aromatic heterocyclic amines—are available by this route. Furthermore, as mentioned above, hetero-aromatic quaternary amine groups have been shown to possess beneficial properties in fully unsaturated psoralens. Thus, a need exists for a facile synthetic route to manufacture such quaternary amine-containing 4',5'-dihydropsoralens.

Manufacturing the commercial psoralen, trioxsalen (1) (4,5',8-trimethylpsoralen or TMP), involves alkene bromination in chloroform of the unsaturated allylic bond in 4,8-dimethyl-6-allyl-7-acetoxycoumarin (3, R=H, R'=Ac). However, if the 7-hydroxyl is not acetylated prior to bromination of the allyl moiety, bromination on C#3 occurs simultaneously with addition of the bromine to the double bond yielding 3-bromo-6-(2,3-dibromopropyl)-4,8-dimethyl-7-hydroxycoumarin (4, R=Br, R'=H).

(3)

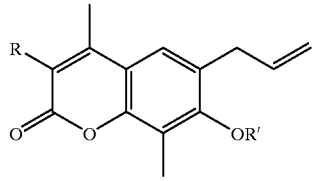

(4)

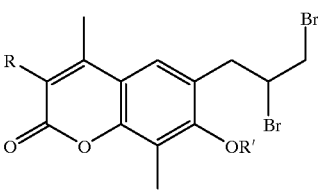

(1)

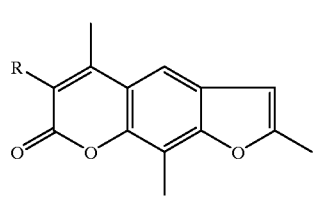

or trioxsalen, R = H

In the Kaufman process, the 6-(2,3-dibromopropyl)-4,8-dimethyl-7-acetoxycoumarin (4, R=H, R'=Ac) is ring-closed by uncapping the 7-acetoxy with sodium ethoxide with concomitant cyclization and double dehydrobromination yielding TMP in 48% yield. See K. D. Kaufman, *J. Org. Chem.*, 1961, 26, 117–121. This reaction involves the loss of two molar equivalents of HBr. Theoretically, this might occur in two separable distinct steps in which one HBr loss is followed by a second through a possible intermediate such as 4,8-dimethyl-4',5'-dihydro-5'-bromomethyl-psoralen (5, R=H, T=Br).

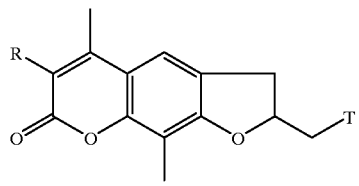

(5)

As noted above, this theoretically possible intermediate is the very target compound which could not be obtained despite numerous attempts by catalytic hydrogenation or exchange hydrogenation to reduce 4,8-dimethyl-5'-bromomethylpsoralen to 4,8-dimethyl-4',5'-dihydro-5'-bromomethylpsoralen; hydrogenolysis to (1) being the dominant outcome. Alas, careful duplication of Kaufman's synthesis revealed no trace of 4,8-dimethyl-4',5'-dihydro-5'-bromomethyl-psoralen (5, T=Br), even as a potential transient. NMR analysis of commercially available TMP prepared by Kaufman's route similarly showed none of this 4',5'-dihydro-5'-bromomethyl material as a contaminant. A ready synthesis of this and other valuable intermediates to prepare quaternary ammonium 4',5'-dihydropsoralens remains as a currently unmet need in the art.

SUMMARY OF THE INVENTION

The invention provides a 5'-substituted, 4,8-dimethyl-4',5'-dihydropsoralen of formula (5):

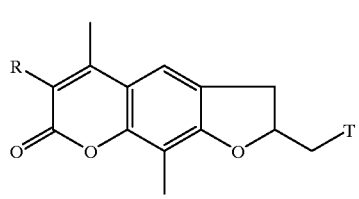

(5)

wherein
R is hydrogen, a halogen, $NO_2$, or CN;
T is a halogen, $NR^1R^2$, $(N^+R^1R^2R^3)X^-$, or $HgR^4$;
$R^1$ and $R^2$ are independently a $C_1$–$C_6$ alkyl, or $R^1$ and $R^2$ together with the nitrogen form a 5–8 member heterocyclic ring, or when T is $(N^+R^1R^2R^3)X^-$, $R^1$ and $R^2$ together with the nitrogen form a 5–8 member heterocyclic ring or heterocyclic aromatic ring;
$R^3$ is hydrogen, a $C_1$–$C_{12}$ alkyl, or, when $R^1$ and $R^2$ together with the nitrogen form a heterocyclic aromatic ring, $R^3$ is a double bond within the heterocyclic aromatic ring;
$X^-$ is a halide;
$R^4$ is $OC(O)(C_1$–$C_6$ alkyl), $OC(O)(C_1$–$C_6$ fluoroalkyl), or a halogen;

with the proviso that the 5'-substituted, 4,8-dimethyl-4'5'-dihydropsoralen is not 4,8-dimethyl-5'-(N-pyridiniummethyl)-4',5'-dihydropsoralen iodide salt.

The invention also relates to a process for preparing a 5'-substituted, 4,8-dimethyl-4',5'-dihydropsoralen of formula (5):

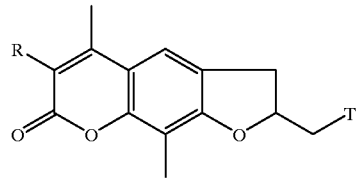

(5)

wherein R and T are as defined above. The process comprises the step of contacting a 4,8-dimethyl-6-allyl-7-hydroxycoumarin of the formula:

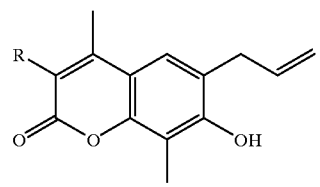

with a cyclization reagent under conditions to form said 5'-substituted, 4,8-dimethyl-4',5'-dihydropsoralen. When T is Br, the cyclization reagent is selected from N-bromosuccinimide. When T is I, the cyclization reagent is selected from N-iodosuccinimide, $I_2$, ICl, and IBr. When T is $HgR^4$, where $R^4$ is $R^4$ is $OC(O)(C_1$–$C_6$ alkyl), $OC(O)(C_1$–$C_6$ fluoroalkyl), or a halogen, the cyclization reagent is $Hg(R^4)_2$.

The invention also provides a process for preparing a 3-R-4,8-dimethyl-4',5'-dihydro-5'-bromomethylpsoralen (5) having the formula:

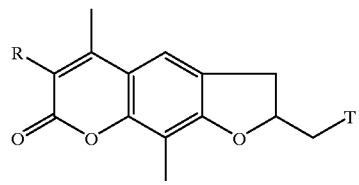

(5)

where T is Br. This method comprises the steps of brominating a compound of formula

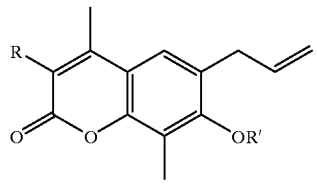

(3)

where R' is acetyl to form 4,8-dimethyl-6-(2,3-dibromopropyl)-7-acetoxycoumarin (4)

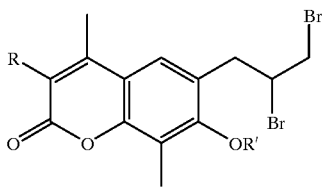

(4)

and cyclizing the resulting 3-R-4,8-dimethyl-6-(2,3-dibromopropyl)-7-hydroxycoumarin to yield the compound (5).

To prepare 5-N-aminomethyl substituted 4,8-dimethyl-4', 5'-dihydropsoralen of the formula (5):

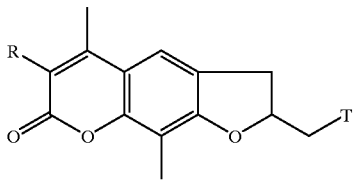

(5)

where R is hydrogen, a halogen, $NO_2$, or CN and T is $NR^1R^2$ or $(N^+R^1R^2R^3)X^-$, one method of the invention contacts a compound of formula (5) where T is Br or I with a secondary amine of the formula of $HNR^1R^2$ or $N^+R^1R^2R^3$. In these amines $R^1$ and $R^2$ are independently a $C_1$–$C_6$ alkyl, or $R^1$ and $R^2$ together with the nitrogen form a 5–8 member heterocyclic ring, or when T is $(N^+R^1R^2R^3)X^-$, $R^1$ and $R^2$ together with the nitrogen form a 5–8 member heterocyclic ring or a 6-member heterocyclic aromatic ring; $R^3$ is hydrogen, a $C_1$–$C_{12}$ alkyl, or, when $R^1$ and $R^2$ together with the nitrogen form a heterocyclic aromatic ring, $R^3$ is a double bond within the heterocyclic aromatic ring; and $X^-$ is bromo or iodo.

In another embodiment, the invention relates to a 2-substituted mercurimethyl-2-3-dihydrobenzofuran of the forumla (7):

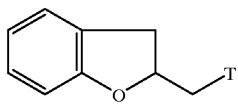

(7)

wherein T is a mercurial group $HgR^4$ and $R^4$ is $OC(O)$ ($C_1$–$C_6$ alkyl), $OC(O)(C_1$–$C_6$ fluoroalkyl), or a halogen. Preferably, $R^4$ is $OC(O)CH_3$, $OC(O)CF_3$, Cl, Br, or I.

The 2-substituted mercurimethyl-2-3-dihydrobenzofuran of forumla (7) according to the invention may be prepared by contacting 2-allylphenol with a cyclization reagent selected from $Hg(R^4)_2$ where $R^4$ is $OC(O)(C_1$–$C_6$ alkyl), $OC(O)(C_1$–$C_6$ fluoroalkyl), or a halogen under conditions to form a 2-substituted mercurimethyl-2-3-dihydrobenzofuran. Accordingly, the invention also relates to a process for preparing a 2-substituted mercurimethyl-2-3-dihydrobenzofuran of forumla (7) as described above.

The compounds of the invention have beneficial pharmaceutical properties and can be used alone or in pharmaceutical compositions used to treat a proliferative skin disorder and to treat microbial infections in a mammal by administering to the mammal an effective amount of a compound of the invention and then irradiating the mammal with ultraviolet light.

Similarly, compounds of the invention and pharmaceutical compositions containing them may be used to treat a disease of the blood or bone marrow or to treat microbial infections in a mammal. Such a method comprising the steps of: obtaining cells from the blood or marrow of the mammal, introducing in vitro into the cells an effective amount of a compound according to the invention, exposing the cells containing the compound to ultraviolet radiation, and returning the cells to the blood or bone marrow of the mammal. For the mercurio-substituted compounds of the invention, the irradiation step is optional.

The compounds of the invention also have anti-microbial properties and can be used to control the growth of microorganisms on substrates and in aqueous systems.

DETAILED DESCRIPTION

1. Compounds of the Invention

This invention relates to 5'-substituted, 4,8-dimethyl-4', 5'-dihydropsoralens of the formula:

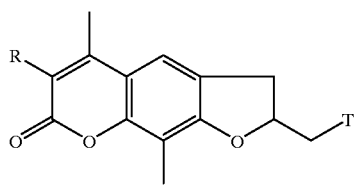

(5)

In formula (5), the substituent R at the 3-position is hydrogen, a halogen, $NO_2$, or CN. In a preferred embodiment, R is hydrogen, F, Br, I, $NO_2$, or CN.

The 5' substituent, T, may be a halogen, an amine of the formula $NR^1R^2$ or $(N^+R^1R^2R^3)X^-$, or a mercurial group $HgR^4$. When T is a halogen, Br and I are preferred.

When T is an amine of the formula $NR^1R^2$, $R^1$ and $R^2$ are independently a $C_1$–$C_6$ alkyl, or $R^1$ and $R^2$ together with the nitrogen form a 5–8 member heterocyclic ring. An alkyl, according to the invention, may be straight chain or branched, substituted or unsubstituted with common substituents such as hydroxyl, halo, nitro, sulfonyl, nitro, amino, etc. The heterocyclic ring may likewise be substituted or unsubstituted. Preferably, $R^1$ and $R^2$ are independently methyl, ethyl, hydroxyethyl, or propyl, or $R^1$ and $R^2$ together with the nitrogen form a heterocyclic ring selected from N-pyrrolidinyl, N-2-pyrrolidinonyl, N-pyrrolinyl, N-pyrazolidinyl, N-pyrazolinyl, N-pyrazolyl, N-imidazolidinyl, N-imidazolinyl, N-imidazolyl, N-oxazolidinonyl, N-piperidinyl, N-piperazinyl, N-morpholinyl, N-pyridinyl, N-4-($C_1$–$C_4$ alkyl)pyridinyl, N-hexamethyleneiminyl, N-heptamethyleneiminyl, N-quinolinyl or N-isoquinolyl. Most preferably, $R^1$ and $R^2$ are independently methyl, 2-hydroxyethyl, or propyl, or $R^1$ and $R^2$ together with the nitrogen form a heterocyclic ring selected from N-morpholinyl, N-pyridinyl, N-4-ethylpyridinyl, N-methylpyridinyl, or N-quinolinyl.

In dihydropsoralens of formula (5) when T is $(N^+R^1R^2R^3)$ $X^-$, $R^1$ and $R^2$ together with the nitrogen form a 5–8 member heterocyclic ring or heterocyclic aromatic ring, as just discussed. When T is $(N^+R^1R^2R^3)X^-$, $R^1$ and $R^2$ have the same preferred embodiments as when T is $NR^1R^2$. $R^3$ is hydrogen, a $C_1$–$C_{12}$ alkyl, or, when $R^1$ and $R^2$ together with the nitrogen form a heterocyclic aromatic ring, $R^3$ is a double bond within the aromatic ring and $X^-$ is a halide. Preferably, $R^3$ is hydrogen, methyl, ethyl, or dodecyl and $X^-$ is a bromide or iodide. Most preferably, $R^3$ is hydrogen, methyl, or dodecyl.

As mentioned, the 5'-substituent T may also be a mercurial group $HgR^4$. In that mercurial group, $R^4$ is $OC(O)(C_1-C_6$ alkyl), $OC(O)(C_1-C_6$ fluoroalkyl), or a halogen. Preferably, $R^4$ is $OC(O)CH_3$, $OC(O)CF_3$, Cl, Br, or I.

Examples of dihydropsoralen compounds of formula 5 are:
4,8-Dimethyl-5'-(bromomethyl)-4',5'-dihydropsoralen;
4,8-Dimethyl-5'-(iodomethyl)-4',5'-dihydropsoralen;
4,8-Dimethyl-5'-(N-pyridiniummethyl)-4',5'-dihydropsoralen bromide salt;
4,8-Dimethyl-5'-(N-4-ethylpyridiniummethyl)-4',5'-dihydropsoralen bromide salt;
4,8-Dimethyl-5'-(N-quinoliniummethyl)-4',5'-dihydropsoralen bromide salt;
4,8-Dimethyl-5'-(N,N,N-trimethylammonium methyl)-4',5'-dihydropsoralen bromide salt;
3-Bromo-4,8-Dimethyl-5'-(bromomethyl)-4',5'-dihydropsoralen;
3-Bromo-4,8-Dimethyl-5'-(iodomethyl)-4',5'-dihydropsoralen;
3-Bromo-4,8-dimethyl-5'-(N-pyridiniummethyl)-4',5'-dihydropsoralen, bromide salt;
3-Bromo-4,8-dimethyl-5'-(N-4-ethylpyridiniummethyl)-4',5-dihydropsoralen, bromide salt;
3-Bromo-4,8-dimethyl-5'-(N-pyridiniummethyl)-4',5'-dihydropsoralen, iodide salt;
3-Bromo-4,8-dimethyl-5'-(N-quinoliniummethyl)-4',5'-dihydropsoralen, bromide salt;
3-Bromo-4,8-dimethyl-5'-(N,N,N-trimethylammoniummethyl)-4',5'-dihydropsoralen, bromide salt;
3-Bromo-4,8-dimethyl-5'-(N,N,N-trimethylammoniummethyl)-4',5'-dihydropsoralen, iodide salt;
3-Nitro-4,8-dimethyl-5'-(bromomethyl)-4',5'-dihydropsoralen;
3-Nitro-4,8-dimethyl-5'-(N-pyridiniummethyl)-4',5'-dihydropsoralen, bromide salt;
3-Nitro-4,8-dimethyl-5'-(N-4-ethylpyridiniummethyl)-4',5'-dihydropsoralen bromide salt;
3-Nitro-4,8-dimethyl-5'-(N-quinoliniummethyl)-4',5'-dihydropsoralen, bromide salt;
3-Nitro-4,8-dimethyl-5'-(N,N,N-trimethylammonium methyl)-4',5'-dihydropsoralen bromide salt;
3-Cyano-4,8-dimethyl-5'-(bromomethyl)-4',5'-dihydropsoralen;
3-Cyano-4,8-dimethyl-5'-(iodomethyl)-4',5'-dihydropsoralen;
3-Cyano-4,8-dimethyl-5'-(N-pyridiniummethyl)-4',5'-dihydropsoralen, bromide salt;
3-Cyano-4,8-dimethyl-5'-(N-pyridiniummethyl)-4',5'-dihydropsoralen, iodide salt;
3-Cyano-4,8-dimethyl-5'-(N-4-ethylpyridiniummethyl)-4',5'-dihydropsoralen bromide salt;
3-Cyano-4,8-dimethyl-5'-(N,N,N-trimethylammoniummethyl)-4',5'-dihydropsoralen bromide salt;
3-Cyano-4,8-dimethyl-5'-(N,N,N-trimethylammoniummethyl)-4',5'-dihydropsoralen iodide salt;
3-Fluoro-4,8-dimethyl-5'-(bromomethyl)-4',5'-dihydropsoralen;
3-Fluoro-4,8-dimethyl-5'-(iodomethyl)-4',5'-dihydropsoralen;
3-Fluoro-4,8-dimethyl-5'-(N-pyridiniummethyl)-4',5'-dihydropsoralen, bromide salt;
3-Fluoro-4,8-dimethyl-5'-(N-4-ethylpyridiniummethyl)-4',5'-dihydropsoralen bromide salt;
3-Fluoro-4,8-dimethyl-5'-(N-quinoliniummethyl)-4',5'-dihydropsoralen, bromide salt;
3-Fluoro-4,8-dimethyl-5'-(N,N,N-trimethylammonium methyl)-4',5'-dihydropsoralen bromide salt;
3-Fluoro-4,8-dimethyl-5'-iodomethyl-4',5'-dihydropsoralen;
3-Iodo-4,8-dimethyl-5'-iodomethyl-4',5'-dihydropsoralen;
3-Fluoro-4,8-dimethyl-5'-acetomercurimethyl-4',5'-dihydropsoralen;
3-Iodo-4,8-dimethyl-5'-acetomercurimethyl-4',5'-dihydropsoralen;
4,8-Dimethyl-5'-acetomercurimethyl-4',5'-dihydropsoralen;
4,8-Dimethyl-5'-trifluoroacetomercurimethyl-4',5'-dihydropsoralen;
4,8-Dimethyl-5'-chloromercurimethyl-4',5'-dihydropsoralen;
4,8-Dimethyl-5'-iodomercurimethyl-4',5'-dihydropsoralen;
3-Cyano-4,8-dimethyl-5'-acetomercurimethyl-4',5'-dihydropsoralen;
3-Fluoro-4,8-dimethyl-5'-acetomercurimetbyl-4',5'-dihydropsoralen;
4,8-Dimethyl-5'-(N,N-diethanolaminomethyl)-4',5'-dihydropsoralen;
4,8-Dimethyl-5'-(N,N-dimethylaminomethyl)-4',5'-dihydropsoralen hydroiodide salt;
4,8-Dimethyl-5'-(N-morpholinomethyl)-4',5'-dihydropsoralen; and
4,8-Dimethyl-5'-(N-2,6-dimethylmorpholinomethyl)-4',5'-dihydropsoralen.

The photochemotherapeutic and/or chemotherapeutic compounds of the invention also include physiologically acceptable salts of the compounds of formula 5. Preferred physiologically acceptable salts are acid-addition salts. Common acceptable acid-addition salts include but are not limited to hydroiodic and hydrochloric acid salts, oxalate salts and tartrate salts.

The invention also relates to a 2-substituted mercurimethyl-2-3-dihydrobenzofuran of the forumla (7):

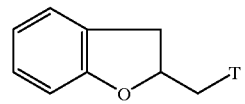

(7)

wherein T is a mercurial group $HgR^4$ wherein $R^4$ is $OC(O)(C_1-C_6$ alkyl), $OC(O)(C_1-C_6$ fluoroalkyl), or a halogen. Preferably, $R^4$ is $OC(O)CH_3$, $OC(O)CF_3$, Cl, Br, or I. A 2-substituted mercurimethyl-2-3-dihydro-benzofuran according to the invention also includes physiologically acceptable salts of the compounds of formula 7. Preferred physiologically acceptable salts are acid-addition salts as described above.

2. Preparation of Compounds of the Invention

The compounds of the invention may be prepared according to general synthetic procedures. The examples below demonstrate the general synthetic procedures, as well as the specific preparation, of 5'-substituted, 4',5'-dihydropsoralen and 2-substituted mercurimethyl-2-3-dihydro-benzofuran compounds according to this invention. The examples are illustrative, and are not intended to limit in any manner, the claimed invention.

Preparation of T=Bromo Derivatives via Allyl Bromination

One embodiment of the invention relates to a 3-R-4,8-dimethyl-4',5'-dihydro-5'-bromomethylpsoralen (5, T=Br) having the formula:

(5)

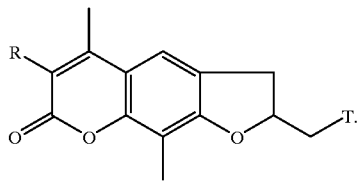

This process comprises the steps of brominating a compound of formula (3, R'=Ac)

(3)

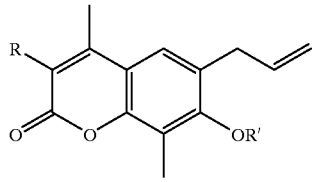

to form 4,8-dimethyl-6-(2,3-dibromopropyl)-7-acetoxycoumarin (4, R=H, R'=Ac) and (4)

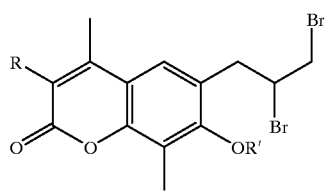

cyclizing to form a mono-dehydrohalogenated dihydro psoralen intermediate (5, R=H, T=halo). Ring closure may be effected by the use of anhydrous sodium carbonate in dry acetone. The 7-acetoxycoumarin (4, R=H, R'=Ac) should first be deacetylated with sodium borohydride before cyclization to (5, R=H, T=Br). Freeing the 7-hydroxyl from the 7-acetoxy is not a trivial achievement. As shown in Example 8 below, treatment with sodium borohydride successfully freed the 7-hydroxyl from the 7-acetoxy compound. Attempted deblocking by promoting an ester interchange with 0.2% p-toluenesulfonic acid in methanol at reflux for 4 hours returned starting material. Aqueous base (1% NaOH in water) at reflux for 7 days gave a complex inseparable yellow-brown oily mixture. When the 7-acetoxy was slurried with anhydrous silica gel in refluxing methanol for 4 hours it was recovered unchanged.

The unacetylated compound (4, R=Br, R'=H), of course, needs no unblocking and cyclizes directly with anhydrous sodium carbonate in acetone in high yield to (5, T=Br). Careful examination of the $^1$H-NMR spectra revealed that cyclizations of (4) yielded 4:1 mixtures of the desired psoralen (5, R=H or Br, T=Br) and the six-membered bromobenzodipyranone isomer (6, R=H or Br). Chromatographic separation was possible, as noted in Example 8, but, as discussed below, was unnecessary for subsequent amination.

(6)

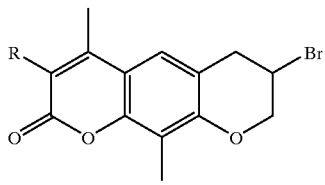

Attempting direct bromination-addition of the double bond without concomitant bromination-substitution at C#3 failed. Lower reaction temperatures, more dilute bromine concentrations, and solvent variations were unsuccessfully explored. Unless the phenolic hydroxy was first acetylated, concomitant bromination at C#3 could not be avoided. However, access to such ring-brominated dihydro quaternary psoralens is a marked synthetic advantage since bromo-substituted psoralens have recently shown promise as photoviricides (see S. Rai)

Preparation of T=Br and I Derivatives via Allyl Cyclization

In another embodiment, 5'-substituted, 4,8-dimethyl-4',5'-dihydropsoralens of formula 5 may be prepared by contacting a 4,8-dimethyl-6-allyl-7-hydroxycoumarin of the formula:

(3)

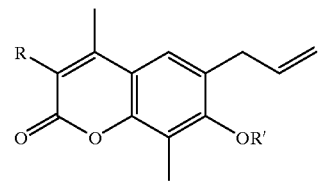

with a cyclization reagent under conditions to form a 5'-substituted, 4,8-dimethyl-4',5'-dihydropsoralen, 5 as represented by the following reaction Scheme 3:

Scheme 3

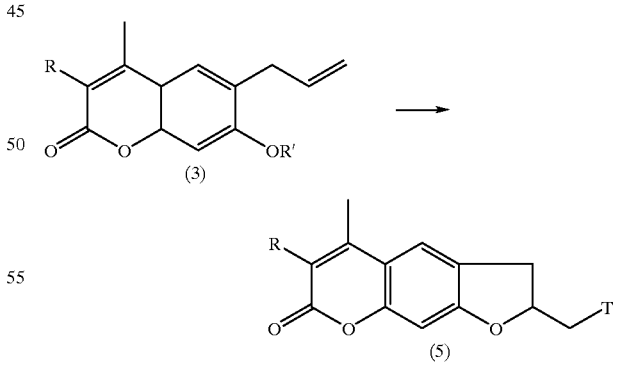

The cyclization reagent used in a process of the invention differs for different substituents T. For example, when T is Br, the cyclization reagent is selected from N-bromosuccinimide and when T is I, the cyclization reagent is selected from N-iodosuccinimide, $I_2$, ICl, and IBr. Preferred processes are shown in Scheme 4 and described in more detail below and in the examples.

Scheme 4

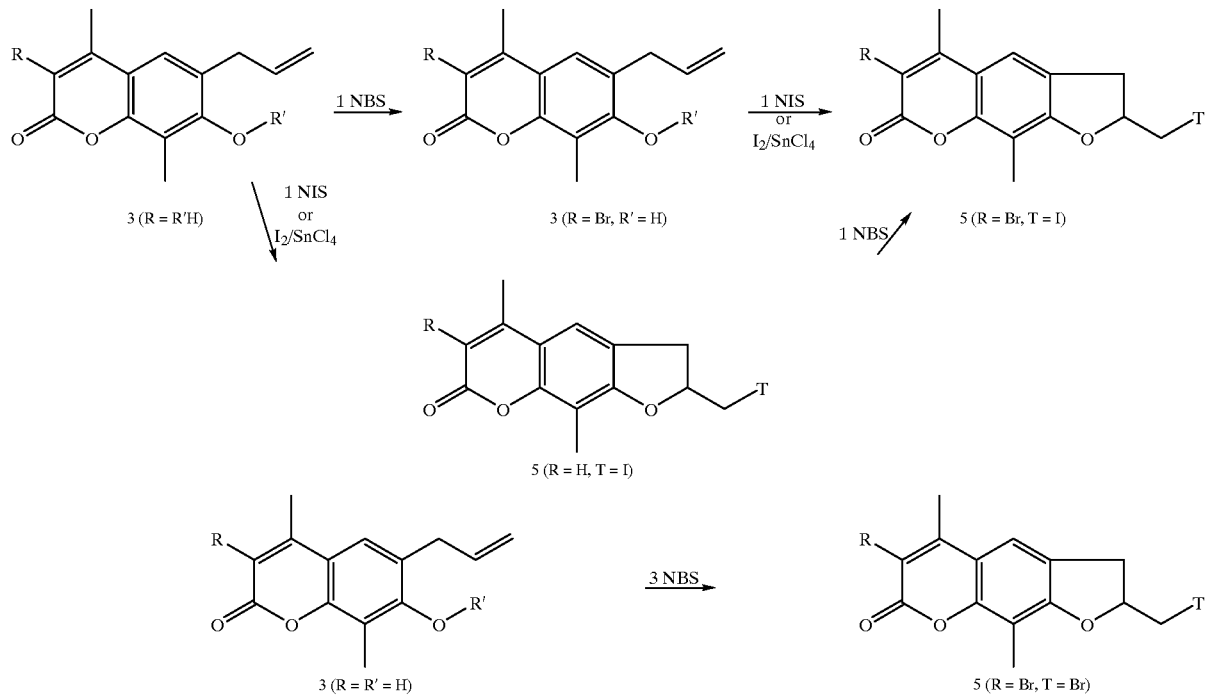

Because as noted above, the bromine facilitated cyclization route on the 4,8-dimethyl-6-allyl-7-hydroxycoumarin 3, (R'=H) lead to benzopyran formation in addition to the desired dihydrofuran formation, alternative electrophiles were explored in the halocyclization reaction to form the dihydrofuran portion of the psoralen ring with higher regioselectivity. Regiospecific bromination-cyclization was achieved by use of three molar equivalents of NBS. This synthesis of 3-bromo-4,8-dimethyl-5'-bromomethyl-4',5'-dihydropsoralen (5, R=Br, T=Br) from 4,8-dimethyl-6-allyl-7-hydroxycoumarin (3, R=H, R'=H), used 3 moles of N-bromosuccinimide (NBS) to selectively brominate the 3-position and ring close to the dihydrofurocoumarin in high yields with the absence of the benzopyran formation, a significant advantage. Variations in temperature (from −80° C. to 25° C.) and the presence or absence of light did not affect this reaction. One mole of NBS in chloroform or one mole of pyridinium hydrobromide perbromide in acetic acid selectively substituted on 4,8-dimethyl-6-allyl-7-hydroxycoumarin (3, R=H , R'=H) to give 3-bromo-4,8-dimethyl-6-allyl-7-hydroxycoumarin (3, R=Br, R'=H), previously generated by the addition of bromine from one mole of Br$_2$. No ring closures occurred under these conditions.

Alternate routes to the 4,8-dimethyl-4',5'-dihydro-5'-halomethylfurocoumarin ring system (some with 3-position substitutions) were also developed. One preferred route involved the use of N-iodosuccinimide (NIS), to selectively ring close 4,8-dimethyl-6-allyl-7-hydroxycoumarin (3, R=H, R'=H), to the 4,8-dimethyl-5'-iodomethyl-4',5'-dihydropsoralen (5, R=H, T=I) in a single step with the absence of benzopyran formation and absence of halogenation at the 3-position. The 3-iodo-4,8-dimethyl-5'-iodomethyl-4',5'-dihydropsoralen (5, R=I, T=I) may be generated by reacting 4,8-dimethyl-5'-iodomethyl-4',5'-dihydropsoralen (5, R=H, T=I) with ICl in acetic acid at 50° C. overnight.

A second preferred route to the 4,8-dimethyl-5'-iodomethyl-4',5'-dihydropsoralen (5, R=H, T=I) by tin (IV) chloride assisted iodocyclization was based on the synthesis of the 5-iodobenzofurans from 2-allyl phenol. The reaction occurs regioselectively in a 5-exo-Trig type cyclization. Applied to psoralen synthesis, this route gave the similar advantage of the NBS and NIS cyclizations in that reactions proceed in high yield with no competing benzopyran formation. Additional iodinating reagents used to successfully ring-close include iodine/NaHCO$_3$/CH$_3$CN, ICl/CH$_2$Cl$_2$ (prone to halogen exchange and to multiple reaction products) and IBr/CH$_2$Cl$_2$ (also prone to multiple products). Attempts to ring close using N-chlorosuccinimide failed.

The bromine- and iodine-based allylcyclization reactions of the invention offer new methods for the synthesis of readily substituted dihydropsoralens to form tertiary amines or quats.

Nitration at the at C#3 of psoralen (5, R=H, T=Br) [in mixture with its six-membered bromobenzodipyranone (6, R=H)] was achieved with concentrated nitric acid in glacial acetic acid giving 3-nitro-4,8-dimethyl-5'-bromomethyl-4',5'-dihydropsoralen (5, R=NO$_2$, T=Br) and nitration product(s) of (6, R=H). Through recrystallization of the mixture, pure (5, R=NO$_2$, T=Br) was obtained in 66% yield. One can note that nitration of (5, R=H, T=Br) at the C#5 seems to not proceed. Finally, the bromide salt (5, R=NO$_2$, T=pyridinium Br salt) was prepared in 69% yield by refluxing (5, R=NO$_2$, T=Br) in anhydrous pyridine.

While the nitro and the bromo substituents at C#3 of psoralen (5, R=NO$_2$ or Br, T=Br) were introduced directly from coumarin or psoralen precursors, the cyano and fluoro group were incorporated at an earlier stage in the synthetic design. See Scheme 5.

Scheme 5

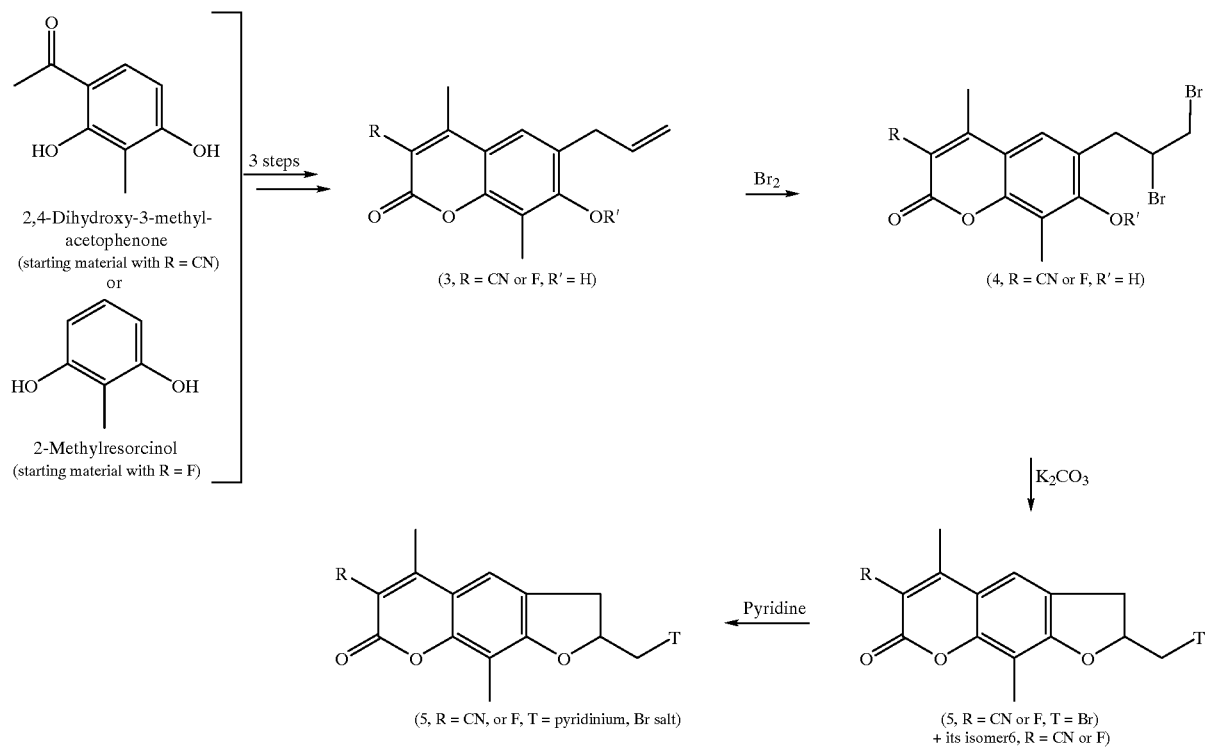

As shown in Example 12, 3-Cyano-4,8-dimethyl-6-allyl-7-hydroxycoumarin (3, R=CN, R'=H) was prepared in 3 steps from 2,4-dihydroxy-3-methylacetophenone through a Knoevenagel condensation with ethyl cyanoacetate as the nitrile carrier (42% overall yield). Then, in a similar fashion to the preparation of the 3-bromopsoralen derivatives, their 3-cyano counterparts were obtained by initial bromination of the allyl double bond [92% of (4, R=CN, R'=H)] and subsequent cyclization with sodium carbonate in acetone to a 78% yield of a 90:10 mixture of 3-cyano-5'-bromomethyldihydropsoralen (5, R=CN, T=Br) and its pyrano isomer (6, R=CN). Pure target compound (5, R=CN, T=pyridinium, Br salt) was obtained in 88% yield from the above 90:10 mixture. The 3-cyano-4,8-dimethyl-5'-iodomethyl -4',5'-dihydropsoralen (5, R=CN, T=I) could be obtained in 71% yield from the NIS ring closure of 3-cyano-4,8-dimethyl-6-allyl-7-hydroxycoumarin (3, R=CN, R'=H). Ring closure is also possible by the $I_2/SnCl_2$ route described above.

Similarly the fluorine atom was introduced during the formation of the pyrone moiety through a Pechmann reaction with ethyl 2-fluoro-acetoacetate as the fluorine carrier. Thus, 3-fluoro-4,8-dimethyl-6-allyl-7-hydroxycoumarin (3, R=F, R'=H) was prepared in 3 steps from 2-methylresorcinol (36% overall yield). Then, ring closure was achieved in two steps in a 66% overall yield following the same route employed with the 3-cyano derivatives giving a mixture 89:11 of (5, R=F, T=Br) and its pyrano isomer (6, R=F) in favor of the expected psoralen. Finally, this 89:11 mixture was reacted with refluxing anhydrous pyridine affording pure target compound (5, R=F, T=pyridinium, Br salt) in 73% yield. Alternatively, the 3-fluoro-6-allyl-7-hydroxycoumarin (3, R=F, R'=H) could be ring closed with NIS in 91% yield to give 3-fluoro-4,8-dimethyl-4',5'-dihydro-5'-iodomethylpsoralen (5, R=F, T=I). The resulting 3-fluoro-4,8-dimethyl-4',5'-dihydro-5'-iodomethylpsoralen was reacted with pyridine to form the pyridinium iodine salt (5, R=F, T=pyridinium iodide). Ring closure of 3-fluoro-6-allyl-7-hydroxycoumarin (3, R=F, R'=H) with mercury acetate in ethanol gave the 5'-acetomercurimethyl-4,8-dimethyl-4',5'-dihydropsoralen (5, R=F, T=HgOAc) in 92% yield.

All of the above allyl cyclization pathways leading to various 3-substituted dihydro psoralens—proceed via highly reactive 5'-bromomethyl-4',5'-dihydro psoralens (5, T=Br) or the 5'-iodomethyl-4',5'-dihydro psoralens (5, T=I). A very useful expansion of that cyclization to other affinity-labeling psoralens is now at hand.

Preparation of T=HgR$^4$X derivatives via Allyl Cyclization

The invention also relates to a process for obtaining 3-R-4,8-dimethyl-4',5'-dihydro-5'-R$^4$mercurimethylpsoralens (5, T=HgR$^4$). According to the invention, 3-R-4,8-dimethyl-4',5'-dihydro-5'-R$^4$mercurimethylpsoralens may be prepared by contacting a 4,8-dimethyl-6-allyl-7-hydroxycoumarin of the formula:

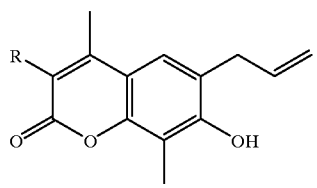

with a cyclization reagent Hg(R$^4$)$_2$ under conditions to form said 5'-substituted, 4,8-dimethyl-4',5'-dihydropsoralen, where R is hydrogen, a halogen, NO$_2$, or CN; and T is HgR$^4$. R$^4$ is OC(O)(C$_1$–C$_6$ alkyl), OC(O)(C$_1$–C$_6$ fluoroalkyl), or a halogen, the cyclization reagent is Hg(R$^4$)$_2$. Preferred substituents R and R$^4$ are the same as those described above. As shown in Example 29, mercury acetate effectively ring closed the 3-cyano-6-allyl-7-hydroxycoumarin (3, R=CN, R'=H) in 80% yield to 3-cyano-4,8-dimethyl-5'-acetomercurimethyl-4',5'-dihydropsoralen (5, R=CN, T=HgOAc). Mercury chloride, however, even with heating did not yield a cyclized product.

Iodomercurimethyl compounds may be prepared by anionic exchange with other 3-R-4,8-dimethyl-4',5'-dihydro-5'-Xmercurimethylpsoralens (e.g. 5, T=HgR$^4$ wherein R$^4$=chloride, trifluoroacetate, acetate) with iodide. Preparing iodomercurimethyl compounds in this manner represents a further embodiment of the invention. Suitable iodide sources include, for example, potassium iodide, sodium iodide, and the like. Suitable mercury-anion derivatives include, for example, HgX with X being aceto, trifluoroaceto, and chloro.

While all the processes and synthetic procedures have been described using 4,8-dimethyl-substituted coumarins, considerable structural variation is, in fact, possible. The classic Pechmann synthesis (R. Elderfield, "Heterocyclic Compounds", II, Wiley & Sons, N.Y., 1951, p. 181 and 251) and the versatile Kostanecki reaction (C. Hauser et al., "Organic Reactions", Vol. 8, 1954, p. 91) are capable of generating a wider variety of different 7-hydroxycoumarins to be employed as starting materials. These 7-hydroxycoumarins may be O-allylated, subjected to the Claisen rearrangement, and may be employed as other examples of $^6$-allyl-7-hydroxycoumarins (viz. 3, R'=H) in the cyclization methods of leading to the 4',5'-dihydropsoralens.

Furthermore, the 7-hydroxycoumarins prepared by Pechmann's or Kostanecki's methods may be nitrated, halogenated, sulphonated, or chloromethylated prior to be subjected to ring closure (i.e. the 3 to 5 pathways). The readily available structural variants of 5 may contain at the dihydropsoralen ring carbon loci numbered 3, 4, 5, 4', and 8, alkyls (e.g., methyl, ethyl, etc.); aryls (e.g., phenyl); alkoxys (e.g., methoxy, ethoxy, etc); aryloxys (e.g., phenoxy); halo groups (F, Cl, Br, I); nitro groups; sulfonyl groups; haloalkyls (e.g., chloromethyl, trifluoromethyl, etc.); sulfonamido groups; amino groups; and alkylamino groups. Accordingly, in another embodiment the invention relates to a process for preparing a 5'-substituted,-4',5'-dihydropsoralen substituted at the 3, 4, 5, 8, or 4' position of formula (8):

(8)

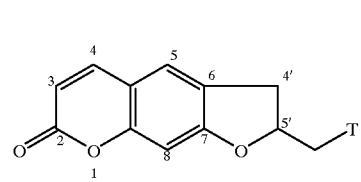

wherein T is a halogen, or HgR$^4$ wherein R$^4$ is OC(O)(C$_1$–C$_6$ alkyl), OC(O)(C$_1$–C$_6$ fluoroalkyl), or a halogen. The process comprises contacting a 6-allyl-7-hydroxycoumarin substituted at the 3, 4, 5, or 8 position of the formula:

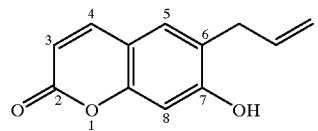

with a cyclization reagent under conditions to form said 5'-substituted, 4',5'-dihydropsoralen substituted at the 3, 4, 5, 8, or 4' position. When T is Br, the cyclization reagent is selected from N-bromosuccinimide; when T is I, the cyclization reagent is selected from N-iodosuccinimide, I$_2$, ICl, and IBr; and when T is HgR$^4$, the cyclization reagent is Hg(R$^4$)$_2$ wherein R$^4$ is as defined above.

Preparation of T=Tertiary Amino and Quaternary Ammonium Derivatives

As shown in the Examples, tertiary amino and quaternary ammonium derivatives of 5'-substituted, 3-R-4,8-dimethyl-4',5'-dihydro-psoralens (5) may be prepared by displacing the bromine or iodine (5, T=Br or I) with an appropriate secondary or tertiary amine. As shown in Example 30, derivatization with pyridine (5, R=CN, T=pyridinium, I salt) occurred in 78% yield from the iodomethyl dihydropsoralen (5, R=CN, T=I) derivative.

As discussed above the unacetylated compound (4, R=Br, R'=H) cyclizes directly with anhydrous sodium carbonate in acetone in high yield to (5, T=Br) but also contained the six-membered bromobenzodipyranone isomer (6, R=H or Br). In general, these cyclizations of (4) yielded 4:1 mixtures of the desired psoralen (5, R=H or Br, T=Br) and the six-membered bromobenzodipyranone isomer (6, R=H or Br). Though possible, chromatographic separation before amination was unnecessary. Because (6) contains a bromine on a secondary carbon and (5) is a primary —CH$_2$—Br system, amination proceeds more rapidly on (5, T=Br) and the only product isolated, under the amination conditions employed, is the quaternary psoralen (5, T=N+, bromide salt).

Some limitations were seen in that the quaternary ammonium derivative from triethylamine did not form and attempts to react the 5'-iodomethyl-4,8-dimethyl-4',5'-dihydrofurocoumarin (5, R=H, T=I) with dodecyl amine did not prove successful. Trimethylpsoralen (1) was recovered when reactions were attempted with 5'-iodomethyl-4, 8-dimethyl-4',5'-dihydrofurocoumarin (5, R=H, T=I) and imidazole, diisopropanolamine, piperidine or an amine in the presence of a strong base in an attempt to force the addition of the amine. Thus, elimination dominated over substitution with more basic nucleophiles.

In a preferred embodiment, 5-N-aminomethyl substituted 4,8-dimethyl-4',5'-dihydropsoralen of the formula (5):

(5)

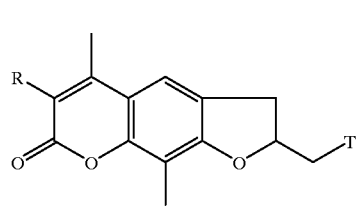

where R is hydrogen, a halogen, NO$_2$, or CN; and T is NR$^1$R$^2$ or (N$^+$R$^1$R$^2$R$^3$)X$^-$ (as defined above) are prepared by contacting a 4,8-dimethyl-6-allyl-7-hydroxycoumarin of the formula:

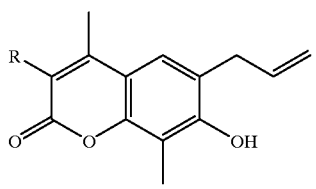

with a cyclization reagent under conditions to form a compound of formula (5) where T is Br or I, and contacting the resulting bromo or iodo compound of formula (5) with a secondary amine of the formula of a secondary amine, $HNR^1R^2$, or a tertiary amine, $NR^1R^2R^3$.

The bromide and iodide anions in the quaternary ammonium salts may be exchanged for other anions (e.g., chloride or another pharmaceutically acceptable anion) by ion exchange on a resin charged with the desired anion.

Preparation of 2-substituted Mercurimethyl-2-3-Dihydrobenzofuran Derivatives

The invention also relates to a process for obtaining 2-substituted mercurimethyl-2-3-dihydrobenzofuran of the forumla (7, $T=HgR^4$). A 2-substituted mercurimethyl-2-3-dihydrobenzofuran according to the invention may be prepared by contacting 2-allylphenol with a cyclization reagent $Hg(R^4)_2$ under conditions to form a 2-substituted mercurimethyl-2-3-dihydrobenzofuran as represented by the following reaction scheme:

(7)

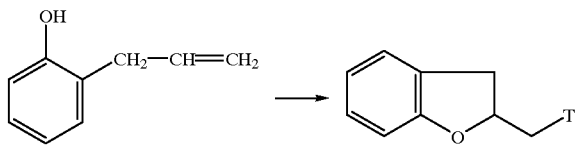

wherein T is a mercurial group $HgR^4$ wherein $R^4$ is OC(O)($C_1$–$C_6$ alkyl), OC(O)($C_1$–$C_6$ fluoroalkyl), or a halogen. Preferably, $R^4$ is $OC(O)CH_3$, $OC(O)CF_3$, Cl, Br, or I. The cyclization reagent is $Hg(R^4)_2$. Preferred substituents R and $R^4$ are the same as those described above. As shown in Example 38, mercury chloride effectively ring closed 2-allylphenol in 89% yield to 2-chloromercurimethyl-2,3-dihydrobenzofuran (7, T=HgCl). Further, as shown in Example 39, mercuric acetate effectively ring closed 2-allylphenol in 60% yield to 2-chloromercurimethyl-2,3-dihydrobenzofuran (7, T=HgOAc).

Iodomercurimethyl-2,3-dihydrobenzofuran compounds may be prepared by anionic exchange with the mercury-anion derivatives of other 2-substituted mercurimethyl-2-3-dihydrobenzofurans (e.g 7, $T=HgR^4$ wherein $R^4$=chloride, trifluoroacetate, acetate) with iodide. Preparing iodomercurimethyl-2,3-dihydrobenzofuran compounds in this manner represents a further embodiment of the invention. Suitable iodide sources include, for example, potassium iodide, sodium iodide, and the like. Suitable mercury-anion derivatives include, for example, HgX with X being aceto, trifluoroaceto, or chloro. As shown in Example 40, anionic exchange of 2-acetomercurimethyl-2,3-dihydrobenzofuran to form 2-iodomercurimethyl-2,3-dihydrobenzofuran occurred in 50% yield.

3. Pharmacological Activity

The 5'-substituted, 4',5'-dihydropsoralens and 2-substituted mercurimethyl-2-3-dihydrobenzofurans according to the invention are photochemotherapeutic compounds, and in the case of the mercurial compounds chemotherapeutic compounds, useful to prevent or treat skin, blood, marrow diseases, and microbial infections in a mammal. Treatment of a disease according to the invention encompasses not only treating an existing condition but treatment to prevent the disease condition from occurring. The partially reduced and quaternized psoralens, amino-substituted psoralens, and mercurio psoralens display impressive photopharmacology against PAM 212 keratinocytes, a model cell line employed as a test system to indicate epidermal cytotoxicity in these candidate photo-therapeutics. Examples of diseases treatable by compounds of the invention include cancer, infections, Acquired Immuno Deficiency Syndrome, HIV, cutaneous T-cell lymphoma, scleroderma, vitiligo, myasthenia gravis, multiple sclerosis, rheumatoid arthritis and other arthridides, psoriasis, inflammation, lupus erythematosus, tuberculosis, and the like.

Compounds of the invention have demonstrated photo-induced activity in an in vitro growth inhibition assay against PAM 212 keratinocytes. Psoriasis, mycosis fungoides, eczema, cancer, and similar proliferative diseases are often characterized by abnormal cell growth regulation. Application of PUVA therapy to correct proliferative disorders on the skin or internally, especially psoriasis, is one clinical expression of photochemotherapy. The use of the assay described in Example 42 is based on the observation that phototherapeutics are extremely potent inhibitors of binding of cell growth in mammalian cells including humans and this inhibition arrests the proliferative disorder. This assay was performed in the cell culture laboratory. For a discussion of cell growth assays see, e.g., J. Laskin et al., Cancer Research 1979, vol. 39, pp. 383–390 and E. Yurkow and J. Laskin, Cancer Chemotherapy and Pharmacology, vol. 27, pp. 315–319, 1991. Inhibition of cell growth is dependent on dose of the phototherapeutic and on the quanta of light in the 320–400 nm wavelength (ultraviolet light A). It is also structure-dependent, that is, there is a direct correlation between those specific phototherapeutics currently used that are clinically active and their ability to inhibit the growth of the cells.

Advantageously, the mercurio-substituted compounds of the invention exhibit chemotherapeutic activity without ultraviolet light activation. The presence of a mercury functionality provides a reactive cell-binding group on these psoralens with unique cytotoxicity without light activation and an up to 2.5-fold enhancement of cytotoxicity activity upon light activation. All non-mercury psoralens required photoactivation to demonstrate any beneficial toxicity.

Accordingly, one embodiment of the invention relates to a method of treatment of a skin disease in a mammal in recognized need thereof. The method comprises administering to the mammal an effective amount of a 5'-substituted, 4',5'-dihydropsoralen or a 2-substituted mercurimethyl-2-3-dihydrobenzofuran and irradiating the mammal with sufficient UVA light to effect photochemical sensitation on the skin. For the mercurio-substituted compounds the irradiation step is optional. The 5'-substituted, 4',5'-dihydropsoralen or 2-substituted mercurimethyl-2-3-dihydrobenzofuran may be administered topically or systemically. Generally, the dosage of UV applied is that conventionally used in the photochemical treatment of skin and preferably ranges from about 0.2 to about 15 joules/cm². The amount and duration of irradiation will depend upon a number of factors including the type and the extent of the disease being treated, the age of the patient, and will be apparent to one skilled in the art. The frequency of treatment will also depend upon such factors and will also be apparent to one skilled in the art.

The 5'-substituted, 4',5'-dihydropsoralens and 2-substituted mercurimethyl-2-3-dihydrobenzofurans of the invention may also be used to treat diseases of the blood or bone marrow in a patient. Accordingly, the invention also relates to a process for the treatment of diseases of the blood or bone marrow in a patient in need of such treatment. The process comprises obtaining cells from the blood or bone marrow of the patient, contacting the cells in vitro with a 5'-substituted, 4',5'-dihydropsoralen according to the invention, exposing the cell in contact with the 5'-substituted, 4',5'-dihydropsoralen with sufficient UVA to activate the therapeutic effect of the 5'-substituted, 4',5'-dihydropsoralen and returning the cell to the patient's blood stream or bone marrow. In another embodiment, the patient is dosed in vivo with the psoralen and the cells of the blood or bone marrow subsequently removed, irradiated ex-vivo, and subsequently returned to the patient.

The compounds of the invention which are capable of intercalating into double-stranded nucleic acid, i.e., 4',5'-dihydropsoralens, may also be used to eliminate or reduce the levels of infectious agents in blood. Blood may be treated with such a compound under the conditions described above and be subsequently irradiated with UVA. This treatment has advantages over known treatments which use psoralen compounds that also form crosslinks in double stranded nucleic acid. In the later case, residual psoralen remaining in the blood sample is potentially quite mutagenic to a patient receiving such blood, e.g., during a transfusion. In the former case, residual 4',5'-dihydropsoralen is potentially far less mutagenic to a recipient of the blood because of the inability of these compounds to form crosslinks in the DNA.

Methods for treating blood cells and marrow are known in the art and taught, for example, by U.S. Pat. No. 5,356,929, the disclosure of which is herein incorporated by reference. Blood cells may be obtained from a patient using any ordinary conventional technique. Bone marrow may be obtained using established protocols available to those in the art and described, for example, in Kitano et al. (1991, Blood 77:1699–1705), or Folks et al (1988, Science 242:919–922). White blood cells may be separated from pigmented cells (red blood cells) and other factors using the common technique of leukopheresis. If necessary, subpopulations of cells of interest from either the blood or bone marrow may be separated from the remainder of cells in the sample using a combination of techniques including centrifugation and flow cytometry. Cells so isolated are then either irradiated (in the case of the patient to whom the drug has already been administered), or they are treated with the compound of choice in a manner similar to that described above for the treatment of cells in culture followed by irradiation. Essentially, the photherapeutic compound is dissolved in isotonic buffered solution and is added to the cells in a therapeutically effective amount to be determined by the extent and type of disease being treated, and the number of cells in the sample. After a period of incubation, treated cells are exposed to ultraviolet light (UVA, 320–400 nm) as described above. In some cases, depending on the compound involved, different wavelengths of light may also be used. After exposure to light, the cells are washed in an isotonic, buffered solution and are returned to either the patient's blood or bone marrow using conventional technology.

The 5'-substituted, 4',5'-dihydropsoralen derivatives and 2-substituted mercurimethyl 2,3-dihydrobenzofuran derivatives according to the invention also have antimicrobial effects. Accordingly, the invention provides a method of treating microbiological infections in a mammal in recognized need thereof. The method comprises administering to the mammal an effective amount of a 5'-substituted, 4',5'-dihydropsoralen derivative or a 2-substituted mercurimethyl 2,3-dihydrobenzofuran derivative according to the invention. Examples of organisms that can be treated by a process according to the invention include *A. Niger*, Chlorella, *Mycobacterium tuberculosis* and fungal organisms, such as dermatophytes, Trichophyton, Microsporum and Epidermophyton, different Candida species, Trichoderma, Cryptococcus, *Aspergillus Zygomyetes*, Fusarim which can cause infections in humans and animals. Histoplasmosis, Blastomyces, and Coccidioides, for example, cause lower respiratory infections. *Trichophyton rubrum* causes difficult to eradicate nail infections. *Hendersonula toruloidea* and *Scopulariopsis brevicaulis* are known to cause tinea pedis, tinea captitis, tinea cruris and different ring worm infections. As shown in Example 44, compounds according to the invention exhibit anti-tuberculosis activity.

Due to their valuable pharmacological properties, the compounds of the invention or their physiologically acceptable salts, are particularly suitable for use as active compounds in pharmaceutical compositions. The 5'-substituted, 4',5'-dihydropsoralens and 2-substituted mercurimethyl-2-3-dihydrobenzofurans of the invention can be either administered alone or in mixtures with one another or with other therapeutic agents. As mentioned above, the 5'substituted, 4',5'-dihydropsoralens and 2-substituted mercurimethyl-2-3-dihydrobenzofurans of the invention may be applied topically in the form of an ointment or lotion, administered orally, intravenously, or parenterally. Methods for preparing clinically-ready compositions are conventional in this art and include gelatin capsules or tablets for oral administration, solutions or ointments for external use, as described, for example, in U.S. Pat. No. 5,356,929. The compounds according to the invention can be administered orally, topically, rectally, anterally, internally, by boluses or, if desired, parenterally. Topical or oral administration may be preferred.

The invention also relates to photochemotherapeutic and chemotherapeutic pharmaceutical compositions for use in treating diseases such as those discussed above. A pharmaceutical composition according to the invention comprises a therapeutically effective amount of a 5'-substituted, 4',5'-dihydropsoralen or a 2-substituted mercurimethyl-2-3-dihydrobenzofuran with or without a pharmaceutically acceptable carrier or agent. Preferably, a pharmaceutical composition according to the invention contains a 5'-substituted, 4',5'-dihydropsoralen or a 2-substituted mercurimethyl-2-3-dihydrobenzofuran in a therapeutically effective amount to treat a disease of the skin, blood or marrow of a mammal, in particular, a human. For treatment of microbiocidal infections, such as tuberculosis, the pharmaceutical composition contains 5'-substituted, 4',5'-dihydropsoralen or a 2-substituted mercurimethyl-2-3-dihydrobenzofuran in a therapeutically effective amount to treat the microbiocidal infection. Pharmaceutically acceptable carriers are known in the art and are described, for example, in U.S. Pat. Nos. 4,124,598 and 4,130,568, the disclosures of which are herein incorporated by reference.

Pharmaceutical compositions of the invention may further include excipient, stabilizers, emulsifiers, therapeutic adjuvants, diluents and the like and may be provided in sustained release or timed release formulations. Suitable solid or liquid formulations are, for example, granules, powders, coated tablets, microcapsules, suppositories, syrups, elixirs, suspensions, emulsions, drops or injectable solutions. Commonly used additives in protracted release preparations are excipients, disintegrates, binders, coating agents, swelling agents, glidants, or lubricants, flavors, sweeteners or solubilizers. More specifically, frequently used additives are, for example, magnesium stearate, magnesium carbonate, titanium dioxide, lactose, mannitol and other sugars, talc, lactalbumin, gelatin, starch, cellulose and its derivatives, animal and vegetable oils, polyethylene glycols and solvents. Common solvents include sterile water and monohydric or polyhydric alcohols such as glycerol. Acceptable carriers, agents, excipient, stabilizers, diluents and the like for therapeutic use are well known in the pharmaceutical field, and are described, for example, in *Remington's Pharmaceutical Sciences*, Mack Publishing Co., ed. A. R. Gennaro (1985). If appropriate, the compound may be administered in the form of a physiologically acceptable salt, for example, an acid-addition salt.

The pharmaceutical compositions are preferably produced and administered in dosage units, each unit containing as an active component an effective dose of at least one compound of the present invention and/or at least one of its physiologically acceptable salts. In the case of mammals, the effective dose to treat diseases such as those discussed above can range from about 1 to about 100 mg/kg of body weight per day.

The pharmaceutical compositions according to the invention are suitable for use in effecting photochemical sensitivity on the skin of a mammal, particularly a human patient or subject, and comprise an effective amount of a 5'-substituted 4',5;-dihydropsoralen or 2-substituted mercurimethyl-2-3-dihydrobenzofurans compound according to the invention and a pharmaceutically acceptable carrier or diluent. Such compositions are well known in the art and taught, for example, by U.S. Pat. Nos. 4,124,598 and 4,130,568, the disclosures of which are herein incorporated by reference.

For oral treatment, the active ingredient is generally formulated in tablets or in gelatin capsules. In such a case, the diluent may, if desired, may be used. For topical applications, solutions or ointments may be prepared and employed. These may be formulated with any one of a number of pharmaceutically acceptable carriers, as is well known in the art. Administration may be, for example, in the form of tablets, capsules, powders, syrups, or solutions, or as already stated in the form of ointments, creams, or solutions for topical use.

For tablet preparation, the usual tablet adjuvants such as cornstarch, potato starch, talcum, magnesium stearate, gelatin, lactose, gums, or the like may be employed, but any other pharmaceutical tableting adjuvants may also be used, provided only that they are compatible with the active ingredient. In general, an oral dosage regimen will include about 5 mg to about 50 mg, preferably from about 5 to about 10 mg, per kg of body weight. Such administration and selection of dosage and unit dosage will of course have to be determined according to established medical principles and under the supervision of the physician in charge of the therapy involved.

Topical formulations comprise an effective amount of the active ingredient per unit area. Preferably, the topical formulation is in the form of a one percent solution, suspension or ointment and is applied on the skin at about 0.1 mL per square centimeter. The formulations contain a suitable carrier, such as, ethanol or any of the pharmaceutically acceptable carriers described above. A typical formulation for a 1% phototherapeutic lotion comprises:

(A) 25 ml of propylene glycol;
(B) 1 ml of triethanolamine;
(C) 12 ml of water;
(D) 1.5 grams of oleic acid;
(E) 10.5 grams of polyethylene glycol 400 monostearate;
(F) 10 ml of silicon fluid DC-200;
(G) 10 ml of CARBOPOL 934, 2% mucilage; and
(H) 1 gram of at least one 5'-substituted, 4',5'-dihydropsoralens according to the invention.

4. Microbicidal Activity and Methods of Use

The 5'-substituted 4',5'-dihydropsoralens according to the invention are useful in preventing the microbiological attack, degradation, or deterioration of various types of raw materials and products such as leather, textiles, plastics, plastic containers, pulp, paper and paperboard, coatings, lumber, as well as agricultural products such as seeds and crops. Antifungal activity of the compounds of the invention were demonstrated by measuring the inhibitory effects of compounds of the invention against *Aspergillis niger*. Antimicrobial activity effects were determined by measuring the inhibitory effects of compounds of the invention against Chlorella with minimum inhibitory concentrations of less than 100 ppm. Advantageously, the 5'-substituted 4',5'-dihydropsoralens and 2-substituted mercurimethyl-2-3-dihydrobenzofurans may be used in various industrial processes used to prepare or manufacture these products. Accordingly, additional embodiments of the invention employ the combination to control the growth of microorganisms on or in such industrial products, raw materials or processes.

Accordingly, another embodiment of the invention provides a microbicidal composition. The composition contains a 5'-substituted, 4',5'-dihydropsoralen or a 2-substituted mercurimethyl-2-3-dihydrobenzofurans in an amount effective to control the growth of at least one microorganism. The invention also provides a method for controlling the growth of a microorganism on a substrate. This method contacts a substrate susceptible to the growth of microorganisms with an effective amount of a 5'-substituted 4',5'-dihydropsoralen or a 2-substituted mercurimethyl-2-3-dihydrobenzofuran to control the growth of at least one microorganism on the substrate. The invention further provides a method for controlling the growth of microorganisms in an aqueous system capable of supporting growth of a microorganism. This method treats the aqueous system with an amount of a 5'-substituted 4',5'-dihydropsoralen or a 2-substituted mercurimethyl-2-3-dihydrobenzofuran effective to control the growth of at least one microorganism in the aqueous system.

Depending on the application, microbicidal compositions according to the invention may be prepared in various forms known in the art. For example, the composition may be prepared in liquid form as an aqueous solution, dispersion, emulsion, or suspension, a dispersion or suspension in a non-solvent, or as a solution by dissolving a 5'-substituted 4',5'-dihydropsoralen in a solvent or combination of solvents. Suitable solvents include, but are not limited to, methyl ethers of glycols, M-pyrol or 1-methyl pyrrolidinone, or petroleum distillates. The microbicidal composition may be prepared as a concentrate for dilution prior to its intended use. Common additives such as surfactants, emulsifiers, dispersants, and the like may be used as known in the art to increase the solubility of the 5'-substituted 4',5'-dihydropsoralen or 2-substituted mercurimethyl-2-3- dihydrobenzofuran in a liquid composition or system, such as an aqueous composition or system.

Microbicidal compositions of the invention may also be prepared in solid form, for example as a powder or tablet, using means known in the art. For example, a liquid product containing a 5'-substituted 4',5'-dihydropsoralen or a 2-substituted mercurimethyl-2-3-dihydrobenzofuran is deposited on carriers such as diatomaceous earth or kaolin. The resulting solid or solids may be mixed together or one solid may be mixed with the other component, or a solution or liquid formulation containing the component, to form a powder or tablet.

According to the invention, control of the growth of a microorganism on a substrate or in an aqueous system means control to, at, or below a desired level and for a desired period of time for the particular substrate or system. This can vary from the complete prevention or inhibition of microbiological growth to control at a certain desired level and for a desired time. The 5'-substituted 4',5'-dihydropsoralens and 2-substituted mercurimethyl-2-3-dihydrobenzofurans described here can, in many cases, reduce the total microbiological count to undetectable limits and maintain the count at that level for a significant period of time. Accordingly, the combination may be used to preserve a substrate or system.

The effective amount or percentage of a 5'-substituted 4',5'-dihydropsoralen or 2-substituted mercurimethyl-2-3-dihydrobenzofurans necessary to achieve the desired result will vary somewhat depending on the substrate or aqueous system to be protected, the conditions for microbial growth, the particular microbicide, and the degree of protection desired. For a particular application, the amount of choice may be determined by routine testing of various amounts prior to treatment of the entire affected substrate or system. In general, an effective amount used on a substrate ranges from about 0.0001% to about 4% (w/w); preferably about 0.0001% to about 1.0%. With aqueous systems, an effective amount may range from about 0.5 to about 10,000 parts per million, more preferably from about 5 to about 5000 parts per million of the aqueous system, and most preferably from, about 10 to about 1000 parts per million. Similar amounts effectively control slime formation. For slime control, effective amounts preferably range from about 1 to about 1000 parts per million, and more preferably, from about 1 to about 200 parts per million of the aqueous system.

A microbicidal composition containing a 5'-substituted 4',5'-dihydropsoralen, 2-substituted mercurimethyl-2-3-dihydrobenzofuran or a mixture thereof may be applied in a variety of industrial uses and processes for microorganism control. The 5'-substituted 4',5'-dihydropsoralens and 2-substituted mercurimethyl-2-3-dihydrobenzofurans may be used in place of and in the same manner as other microbiocides traditionally used in the particular industry. As discussed above, such industries include, but are not limited to the leather industry, the lumber industry, the papermaking industry, the textile industry, the agricultural industry, and the coating industry. The 5'-substituted 4',5'-dihydropsoralens and 2-substituted mercurimethyl-2-3-dihydrobenzofurans may also be used with aqueous systems such as those previously discussed which are subject to microbiological attack and degradation. The problems caused by microbiological attack and deterioration in these various applications has been described above.

EXAMPLES

The following examples demonstrate the preparation of compounds according to the invention. The examples are illustrative, and are not intended to limit, in any manner, the claimed invention.

Example 1

Preparation of 3-bromo-4,8-dimethyl-6-(2,3-dibromopropyl)-7-hydroxycoumarin (4, R=Br, R'=H)

Into a 50 mL round bottom flask equipped with a magnetic stirrer was placed 230 mg (1.00 mmol) of (3, R=H, R'=H) or 4,8-dimethyl-6-allyl-7-hydroxycoumarin (K. D. Kaufman, J. Org. Chem., volume 26, 1961, pp. 117–121) and 10 mL of carbon tetrachloride. To this stirred suspension at ambient temperatures was slowly added in dropwise fashion 240 mg (1.50 mmol) of bromine dissolved in carbon tetrachloride. After the addition was complete (approximately 10 minutes) the flask walls were washed down with additional carbon tetrachloride. The reaction mixture was dark colored at this point and stirring was continued overnight. A white precipitate developed and the customary evolution of HBr (white acidic fumes) was evident. The precipitate was filtered and the crude off-white product upon drying represented 340 mg (0.725 mmol). An analytical thin layer chromatogram performed on silica gel (Whatman) plates with 5% acetone in methylene chloride elutant, gave four well-defined spots at Rf values of 0.46, 0.64, 0.83, and 0.95 with relative intensities of 0.64>0.46>0.95>0.83. Column chromatography on silica gel using 5% acetone in methylene chloride afforded a pure compound (4, R=Br, R'=H) with an Rf of 0.73 under the above reported analytical conditions and an mp of 198.0–198.5° C. (dec.).

Anal. Calcd for $C_{14}H_{13}Br_3O_3$: C, 35.85; H, 2.79. Found: C, 36.38; H, 2.99. IR (1% KBr disc): 3200–3600, 1701 $cm^{-1}$. $^1$H-nmr (DMSO-$d_6$): δ 2.23 (s, 3H), 2.55 (s, 3H), 3.14 (dd, $J_1$=14.3 Hz, $J_2$=9.4 Hz, 1H), 3.46 (dd, $J_1$=14.3 Hz, $J_2$=4.9 Hz, 1H), 3.96 (d, J=5.6 Hz, 2H), 4.67–4.77 (m, 1H), 7.52 (s, 1H), 9.83 (s, 1H); $^{13}$C-nmr (DMSO-$d_6$): δ 8.77, 8.90, 19.43, 53.31, 53.64, 107.92, 111.26, 111.89, 122.67, 125.07, 149.98, 151.99, 156.58, 156.91.

Example 2

Preparation of 3-bromo-4,8-dimethyl-6-allyl-7-hydroxycoumarin (3, R=Br, R'=H)

A mixture of coumarin derivative 4 (R=Br, R'=H) (0.628 g, 1.339 mmoles) and 0.40 g of zinc dust in solution in 35 mL of 95% ethanol was stirred and heated at reflux under an inert atmosphere for 20 minutes. The excess zinc was removed by filtration through a Millipore membrane (0.22 μm filter unit) and the ethanol evaporated under reduced pressure. The resulting solid was recrystallized from a mixture of methanol:water affording 0.330 g (80% yield) of 3 (R=Br, R'=H) as a white solid: mp 158–160° C.

Anal. Calcd. for $C_{14}H_{13}BrO_3 \times 0.2\ H_2O$: C, 53.76; H, 4.32. Found: C, 53.75; H, 4.00. IR (nujol): 3500–3080, 1692 $cm^{-1}$; $^1$H-nmr (CDCl$_3$): δ 2.32 (s, 3H), 2.57 (s, 3H), 3.47 (d, J=6.2 Hz, 2H), 5.18–5.25 (m, 2H), 5.55 (5, 1H), 5.96–6.04 (m, 1H), 7.24 (s, 1H). MS; (EI) m/z 310 (M$^+$, 97) 308 (M$^+$, base), 201 (51), 173 (58), 128 (57), 115 (76), 77 (47).

Example 3

Alternative Preparation of 3-Bromo-4,8-dimethyl-6-allyl-7-hydroxycoumarin (3, R=Br, R'=H).

A mixture of 4,8-dimethyl-6-allyl-7-hydroxycoumarin (3, R=H) (1.25 g, 5.43 mmoles) and N-bromosuccinimide (NBS) (1.2 g, 6.20 mmoles) was added to 50 ML dry tetrahydrofuran with stirring. The mixture was stirred in the dark, at room temperature for 1.5 hours. Saturated potassium sulfite was added and stirring was continued for an additional ten minutes. The THF was evaporated, and solids were taken up in chloroform, washed with brine and dried over $MgSO_4$. The chloroform was evaporated in vacuo to give pale yellow crystals. The product was purified on a silica column using 30% ethyl acetate/70% hexanes, with a yield of 1.29 g (77%) 3-bromo-4,8-dimethyl-6-allyl-7-hydroxycoumarin (3, R=Br, R'=H). The product was further purified by column chromatography on silica gel with 5% MeOH/95% $CDCL_3$ yielding white crystals with a mp of 175.4–175.8° C. TLC on silica gel using 5% MeOH/95% $CDCL_3$ showed a single spot with an Rf of 0.38.

Anal. Calcd for $C_{14}H_{13}BrO_3 \times 0.2\ H_2O$: C, 53.76; H, 4.32. Found: C, 53.75; H, 4.36. $^1$H-nmr ($CDCl_3$): (2.32 (s, 3H), 2.57 (s, 3H), 3.47 (d, J=6.2 Hz, 2H), 5.18–5.25 (m, 2H), 5.55 (s, 1H), 5.96–6.04 (m, 1H), 7.24 (s, 1H).

Example 4
Preparation of 3-Bromo-4,8-dimethyl-5'-bromomethyl-4',5'-dihydropsoralen (5,R=Br, T=Br)

A mixture of 0.50 g (1.07 mmoles) of tribromo 4 (R=Br, R'=H), 50 mL of dry acetone and 5.0 g of oven-dried sodium carbonate were charged to a round bottom flask and refluxed with stirring for four hours and subjected to magnetic stirring for another 12 hours. The carbonate salt was filtered in vacuo, washed on the filter with dry acetone, and the solvent evaporated to yield 0.42 grams (quantitative yield) of buff-yellow compound. Purification was effected by exhaustive trituration with cold acetone and vacuum drying which yielded a purified target compound (single spot Rf=0.69, silica gel TLC, 1% acetone in $CH_2Cl_2$ as eluant), mp 166–167° C. A sample for elemental analysis was prepared by recrystallization from methanol, white needles, mp 178–179° C.

Anal. Calcd for $C_{14}H_{12}Br_2O_3$: C, 43.33; H, 3.12; Br, 41.18. Found: C, 43.30; H, 3.09; Br, 41.17. IR (nujol) 1709 cm$^{-1}$; $^1$H-nmr ($CDCl_3$): δ 2.21 (s, 3H), 2.59 (s, 3H), 3.59 (dq, $J_1$=9.3 Hz, $J_2$=1.3 Hz, $J_3$=1.3 Hz, 2H), 3.82 (dq, $J_1$=10.9 Hz, $J_2$=5.0 Hz, $J_3$=4.9 Hz, 2H), 5.25 (m, 1H), 7.55 (s, 1H). Within the mixture of closure products as generated herein, integration of their respective $C_5H$'s in the furan (i.e., psoralen) isomer and in the pyrano isomer, revealed a 81/19 ratio favoring the expected 4',5'-dihydropsoralen. The $^1$H-nmr spectrum of the minor isomer (19%) was: δ 2.22 (s, 3H), 2.60 (s, 3H), 4.42 (dq, $J_1$=5.5 Hz, $J_2$=1.8 Hz, $J_3$=1.8 Hz, 2H), 4.58 (dq, $J_1$=2.5 Hz, $J_2$=1.4 Hz, $J_2$=1.3 Hz, 2H), 4.84 (m, 1H), 7.48 (s, 1H).

Example 5
Alternative Preparation of 3-Bromo-4,8-dimethyl-5'-bromomethyl-4',5-dihydropsoralen (5, R=Br, T=Br)

4,8-Dimethyl-6-allyl-7-hydroxycoumarin (3, R=H) (2.00 g, 8.68 mmoles) was added to 200 mL of anhydrous THF before the addition of NBS (4.68 g, 26.3 mmoles) in a round bottom flask equipped with stirrer. The mixture was stirred in the dark at room temperature for 1.5 hours. The GC/MS indicated no starting material remained. Saturated sodium bisulfite was added, and stirring continued for ten minutes. The THF was evaporated and solids were taken up in chloroform, washed pith NaCl solution and water, followed by drying over $MgSO_4$. Evaporation of the chloroform layer yielded mustard yellow crystals. The product was recrystallized from methanol. No evidence was seen of the unwanted pyrano isomer, as was found in the molecular bromination route of the 3-bromo-4,8-dimethyl-6-allyl-7-hydroxycoumarin (3, R=Br, R'=H) reported in previous work in this lab (Rapp, unpublished data). The yield was 2.88 g (85%). The compound was purified by column chromatography on silica gel with 5% MeOH/95% $CDCL_3$ to yield tan crystals. TLC using the same solvent showed one spot with an Rf of 0.72. Further recrystallization from methanol gave white crystals with a mp of 182.3–182.5° C.

Anal. Calcd for $C_{14}H_{12}Br_2O_3$: C, 43.33; H, 3.12. Found: C, 43.76; H, 3.08. $^1$H-nmr (DMSO-$d_6$): (2.23 (s, 3H), 2.55 (s, 3H), 3.14 (dd, $J_1$=14.3 Hz, $J_2$=9.4 Hz, 1H), 3.46 (dd, $J_1$=14.3 Hz, $J_2$=4.9 Hz, 1H), 3.96 (d, J=5.6 Hz, 2H), 4.67–4.77 (m, 1H), 7.52 (s, 1H). $^{13}$C-nmr (DMSO-$d_6$): (8.77, 8.90, 19.43, 53.31, 53.64, 107.92, 111.26, 111.89, 122.67, 125.07, 149.98, 151.99, 156.58, 156.91.

Example 6
Preparation of 3-Bromo-4,8-dimethyl-5'-(N-pyridiniummethyl)-4',5'-dihydropsoralen Bromide Salt (5, R=Br, T=pyridinium, Br Salt)

A mixture of 0.204 g (0.525 mmoles) of (5, R=Br, T=Br) and 4.0 mL of anhydrous pyridine were stirred at reflux for 1.5 hours, the pyridine was evaporated in vacuo and the resulting solid washed on a filter with anhydrous ether. This crude product, 0.198 g, 81%, was recrystallized from methanol with the assistance of charcoal decolorization, to yield an off-white crystalline solid, mp 270–270.5° C. (decomp).

Anal. Calcd for $C_{19}H_{17}Br_2NO_3 \times 0.5\ H_2O$: C, 47.93; H, 3.81; N 2.94; Br, 33.56. Found: C, 47.89; H, 3.86; N, 2.88; Br, 33.53. IR (nujol): $^1$H-nmr ($CD_3OD$): δ 2.22 (s, 3H), 2.61 (s, 3H), 3.24–3.31 (m, 1H), 3.68 (dd, $J_1$=16.3 Hz, $J_2$=9.3 Hz, 1H), 4.82–4.92 (m, 1H), 5.10 (dd, $J_1$=13.7 Hz, $J_2$=2.7 Hz, 1H), 5.42–5.61 (m, 1H), 7.58 (s, 1H), 8.20 (dd, $J_1$≈7 Hz, $J_2$≈7 Hz, 2H), 8.68 (dd, $J_1$≈8 Hz, $J_2$≈8 Hz, 1H), 9.09 (d, J=5.5 Hz, 2H).

According to this same procedure one can prepare:

3-Bromo-4,8-dimethyl-5'-(N-4-ethylpyridiniummethyl)-4',5'-dihydropsoralen, bromide salt by displacement of the appropriate (5) with 4-ethylpyridine, 3-Bromo-4,8-dimethyl-5'-(N-quinoliniummethyl)-4',5'-dihydropsoralen, bromide salt by displacement of (5) with quinoline, 3-Bromo-4,8-dimethyl-5'-(N,N,N-trimethylamroniummethyl)-4','-dihydropsoralen, bromide salt by displacement of the appropriate (5) with trimethylamine and similar 3-bromo-4',5'-dihydro-5'-quaternary ammonium methyl psoralens.

Example 7
Preparation of 4,8-Dimethyl-6-(2,3-dibromopropyl)-7-acetoxycoumarin (4, R=H, R'=Ac)

This compound was prepared as described by Kaufman (J. Org. Chem., volume 26, 1961, pp. 117–121)

Example 8
Preparation of 4,8-Dimethyl-5'-bromomethyl-4',5'-dihydropsoralen (5, R=H, T=Br)

A mixture of 0.050 g (0.115 mmoles) of (4, R=H, R'=Ac), 5 mL of anhydrous ethyleneglycol dimethyl ether, and 100 mg of sodium borohydride was stirred and heated at 45° C. for 12 hours. The reaction material was chilled in ice, decomposed by dropwise addition of saturated ammonium chloride solution, 15 mL of $CH_2Cl_2$ were added, and the layers separated. The aqueous layer was washed with 5.0 mL of $CH_2Cl_2$ and the organic phases combined and washed with 2×10 mL of saturated ammonium chloride and 2×10 mL of saturated sodium chloride solution. The organic phase was dried ($MgSO_4$), evaporated in vacuo, and 0.038 g of pale yellow solid was isolated. This solid was purified on a 500 micron prep plate TLC with 5% MeOH in $CH_2Cl_2$ as the moving phase. The "product" spot [a mixture of the isomeric psoralen and benzo-dipyranone] was isolated by elution of the Rf=0.71 band with methanol. Thus 0.023 g (64% yield) of the mixed isomers was obtained.

IR (nujol) 1709 cm$^{-1}$. $^1$H-nmr (CD$_3$OD): δ 2.22 (s, 3H), 2.31 (s, 3H), 3.27 (dq, J$_1$=16.0 Hz, J$_2$=9.1 Hz, J$_3$=6.9 Hz, 2H), 3.54 (dq, J$_1$=10.5 Hz, J$_2$=6.9 Hz, J$_3$=4.4 Hz, 2H), 5.06 (m, 1H), 6.03 (s, 1H), 7.19 (s, 1H). Within the mixture of isomeric closure products generated herein, integration of the C$_3$—H resonances in the respective products revealed a 81/19 ratio favoring the furano (psoralen) product (5, R=H, T=Br) over the benzodipyranone (6, R=H). The $^1$H-nmr spectrum of that minor isomer (the benzodipyranone) was: δ 2.23 (s, 3H), 2.33 (s, 3H), 2.81 (dd, J$_1$=8 Hz, J$_2$=6.5 Hz, 2H), 3.32 (dd, J$_1$=8.0 Hz, J$_2$=6.5 Hz, 2H), 4.97 (m, 1H), 6.01 (s, 1H), 7.15 (s, 1H). Preparative chromatography or tedious recrystallization from cyclohexane/benzene could yield the pure (5, R=H, T=Br) as an off-white solid, mp 126–128° C., but since all subsequent aminations reactions of the unseparated mixture of (5, R=H, T=Br) and (6, R=H) occur only upon the (5) isomer, separation was unnecessary.

Example 9
Preparation of 4,8-Dimethyl-5'-(N-pyridiniummethyl)-4',5'-Dihydropsoralen Bromide Salt (5, R=H, T=pyridinium, Bromide Salt)

A round bottom flask was charged with 0.10 g (0.32 mmoles) of the above 81:19 mixture of (5, R=H, T=Br) and (6, R=H), 2.0 mL of anhydrous pyridine and the reaction mixture stirred at reflux for 16 hours while being protected by a calcium chloride drying tube. The resulting precipitate was collected by suction giving 0.066 g (53% yield) of the pyridinium salt, mp 295.0–295.5° C. (decomp).

Anal. Calcd for C$_{19}$H$_{18}$BrNO$_3$×0.7 H$_2$O: C, 56.93; H, 4.88; N, 3.49; Br, 19.93. Found: C, 56.91; H, 4.55; N, 3.29; Br, 19.83. $^1$H-nmr (CD$_3$OD): δ 2.20 (s, 3H), 2.42 (d, J=0.8 Hz, 3H), 3.26 (dd, J$_1$=16.8 Hz, J$_2$=6.3 Hz, 1H), 3.66 (dd, J$_1$=16.4 Hz, J$_2$=10.2 Hz, 1H), 4.88 (dd, J$_1$=13.6 Hz, J$_2$=9.1 Hz, 1H), 5.11 (dd, J$_1$=13.7 Hz, J$_2$=2.7 Hz, 1H), 5.37–5.47 (m, 1H), 6.15 (d, J=0.8 Hz, 1H), 7.50 (s, 1H), 8.20 (dd, J$_1$=7 Hz, J$_2$≈7 Hz, 2H), 8.68 (dd, J$_1$≈8 Hz, J$_2$≈8 Hz, 1H), 9.09 (d, J=5.5 Hz, 2H).

According to this procedure one can prepare:

4,8-Dimethyl-5'-(N-4-ethylpyridiniummethyl)-4',5'-dihydropsoralen bromide salt by displacement of the requisite (5) with 4-ethylpyridine, 4,8-Dimethyl-5'-(N-quinoliniummethyl)-4',5'-dihydropsoralen bromide salt by displacement of the requisite (5) with quinoline, 4,8-Dimethyl-5'-[(N,N,N-trimethylammonium)methyl]-4',5'-dihydropsoralen iodide salt by displacement of the requisite (5) with trimethylamine (albeit a higher boiling solvent such as ethylene glycol dimethyl ether is required) and similar 4',5'-dihydro-5'-quaternary ammonium methyl psoralens.

Bromide anions in these salts may be exchanged for other anions (e.g., chloride or iodide) by ion exchange on a resin charged with the desired anion.

Example 10
Preparation of 3-Nitro-4,8-dimethyl-5'-bromomethyl-4',5'-dihydropsoralen (5, R=NO$_2$, T=Br)

The above 81:19 mixture (0.201 g, 0.650 mmoles) of (5, R=H, T=Br) and (6, R=H), was dissolved in 3.5 mL of glacial acetic acid and a solution of concentrated nitric acid:glacial acetic acid (25:75; v:v) was added dropwise. The reaction mixture was stirred at room temperature under an inert atmosphere for 5 hours. Water (80 mL) was added, the resulting yellow precipitate was collected by suction filtration and washed with water. Recrystallisation from methanol gave 0.153 g (66% yield) of the 3-nitro compound (5, R=NO$_2$, T=Br) as a yellow solid: mp 187° C. IR (nujol) 1719 cm$^{-1}$; $^1$H-nmr (CDCl$_3$): δ 2.27 (s, 3H), 2.44 (s, 3H), 3.25 (dd, J$_1$=16.2 Hz, J$_2$=6.3 Hz, 1H), 3.48 (dd, J$_1$=16.1 Hz, J$_2$=9.2 Hz, 1H), 3.56–3.68 (m, 1H), 5.14–5.23 (m, 1H), 7.36 (s, 1H); $^{13}$C-nmr (CDCl$_3$): δ 8.56, 14.51, 14.53, 82.52, 82.78, 108.57, 111.32, 119.18, 124.27, 145.62, 152.10, 153.69, 163.12.

Example 11
Preparation of 3-Nitro-4,8-dimethyl-5'-(N-pyridiniummethyl)-4',5'-dihydropsoralen Bromide Salt (5, R=NO$_2$, T=pyridinium, Bromide Salt)

The 5'-Bromomethylpsoralen (5, R=NO$_2$, T=Br) (0.105 g, 0.296 mmoles) was reacted as for (5, R=H, T=pyridinium, bromide salt) using 2 mL of anhydrous pyridine. The resulting precipitate was collected by suction filtration giving 0.089 g (69% yield) of the pyridinium salt (5, R=NO$_2$, T=pyridinium, bromide salt) as a yellow solid: mp 250–251° C. (decomp.).

Anal. Calcd for C$_{19}$H$_{17}$BrN$_2$O$_{5\times0.25}$ H$_2$O: C, 52.13; H, 4.03; N, 6.40. Found: C, 52.13; H, 3.93; N, 6.31. IR (nujol) 3490–3270, 1718 cm$^{-1}$; $^1$H-nmr (CD$_3$OD): δ 2.23 (s, 3H), 2.48 (s, 3H), 3.29–3.30 (m, 1H), 3.70 (dd, J$_1$=16.5 Hz, J$_2$=9.3 Hz, 1H), 4.82–4.92 (m, 1H), 5.12 (dd, J$_1$=13.8 Hz, J$_2$=2.7 Hz, 1H), 5.45–5.55 (m, 1H), 7.70 (s, 1H), 8.21 (dd, J$_1$≈7 Hz, J$_2$≈7 Hz, 2H), 8.69 (dd, J$_1$≈8 Hz, J$_2$≈8 Hz, 1H), 9.10 (d, J=5.6 Hz, 2H).

Example 12
Preparation of 3-Cyano-4,8-dimethyl-5'-bromomethyl-4',5'-dihydropsoralen (5, R=CN, T=Br)

Allyl bromide (2.82 mL, 32.59 mmoles) was added to a mixture of 2,4-dihydroxy-3-methylacetophenone (4.92 g, 29.61 mmoles), ca. 24 g of potassium carbonate, 60 mL of dry acetone and the reaction mixture stirred under an inert atmosphere at room temperature for 16 hours. Then, excess allyl bromide (0.51 mL, 5.89 mmoles) was added, and the reaction mixture was stirred for another 16 hours. The carbonate salt was removed by suction filtration, washed with acetone and the solvent evaporated under reduced pressure. Water (20 mL) was added and the residue was extracted with ether followed by the usual work-up. The crude compound was purified by flash chromatography (mixture hexane:AcOEt; 90:10; v:v; as the eluent) giving 5.25 g (86% yield) of 2-hydroxy-3-methyl-4-allyloxy-acetophenone as a colorless liquid.

$^1$H-nmr (CDCl$_3$): δ 2.11 (s, 3H), 2.54 (s, 3H), 4.57–4.62 (m, 2H), 5.28 (ddd, J$_1$=9.2 Hz, J$_2$=1.4 Hz, J$_3$=1.4 Hz, 1H), 5.40 (ddd, J$_1$=17.2 Hz, J$_2$=1.4 Hz, J$_3$=1.4 Hz, 1H), 5.96–6.09 (m, 1H), 6.40 (d, J=9.0 Hz, 1H), 7.55 (d, J=8.9 Hz, 1H), 12.76 (s, 1H); EIMS m/z (rel int) 206 (M$^+$, 63), 191 (99), 137 (46), 91 (31), 43 (base), 41 (99), 39 (82).

A solution of 2-hydroxy-3-methyl-4-allyloxy-acetophenone (5.60 g, 27.15 mmoles), ethyl cyanoacetate (5.78 mL, 54.31 mmoles), and glacial acetic acid (2.48 mL, 43.32 mmoles) in 30 mL of benzene was heated at reflux in a Dean-Stark apparatus under an inert atmosphere for 6 days. During this time, ammonium acetate (2.10 g, 27.24 mmoles) was added by small portions to the hot solution. The reaction mixture was analyzed by GC/MS (oven temperature: 90° C. for 2 min, then 25° C./min to 300° C.), signals were observed at 6.89 minutes (20%, unreacted 2-hydroxy-3-methyl-4-allyloxy-acetophenone) and 10.01 minutes (80%, 3-cyano-4,8-dimethyl-7-allyloxycoumarin). Thus assuming a 80% conversion, the reaction was cooled at rt. After benzene removal under reduced pressure, chloroform was added and the mixture was washed with water followed by the usual work-up. The crude compound was purified by recrystallization from a mixture of ethanol:water, affording 4.54 g (65% yield) of 3-cyano-4,8-dimethyl-7-allyloxycoumarin as a pale brown solid: mp 172° C.

Anal. Calcd for $C_{15}H_{13}NO_3$: C, 70.58; H, 5.13; N, 5.49. Found: C, 70.29; H, 5.06; N, 5.62. IR (nujol) 2225, 1712 cm$^{-1}$; $^1$H-nmr (CDCl$_3$): δ 2.30 (s, 3H), 2.69 (s, 3H), 4.68 (dd, J$_1$=3.5 Hz, J$_2$=1.5 Hz, 2H), 5.33 (d, J=10.5 Hz, 1H), 5.43 (d, J=17.3 Hz, 5.97–6.10 (m, 1H), 6.89 (d, J=8.9 Hz, 1H), 7.52 (d, J=9.9 Hz, 1H); $^{13}$C-nmr (CDCl$_3$): δ 7.92, 17.81, 69.12, 108.56, 108.82, 111.70, 113.80, 114.62, 117.89, 124.24, 131.55, 152.23, 157.20, 161.68, 161.93; EIMS m/z (rel int) 255 (M$^+$, 94), 214 (27), 41 (base), 39 (39).

A solution of 3-cyano-4,8-dimethyl-7-allyloxycoumarin (1.27 g, 4.97 mmoles) in 14 mL of N,N-diethylaniline was deoxygenated with argon for 30 minutes, and then was heated at reflux for 6 hours, while being purged by bubbling argon through the solution. The reaction mixture was chilled in ice, the resulting precipitate was collected by suction filtration and dried in vacuo. Recrystallisation from a mixture of benzene:methanol gave 0.97 g (76% yield) of 3-cyano-4,8-dimethyl-6-allyl-7-hydroxycoumarin (3, R=CN, R'=H) as a pale brown solid: mp 234–235° C.

Anal. Calcd for $C_{15}H_{13}NO_3$: C, 70.58; H, 5.13; N, 5.49. Found: C, 70.77; H, 4.93; N, 5.46. IR (nujol) 3500–3000, 2224, 1694 cm$^{-1}$; $^1$H-nmr (acetone-d$_6$): δ 2.30 (s, 3H), 2.72 (s, 3H), 3.51 (d, J=6.4 Hz, 2H), 5.02–5.14 (m, 2H), 5.96–6.10 (m, 1H), 7.61 (s, 1H), 8.90 (broad s, 1H).

To a stirred solution of 3-cyano-4,8-dimethyl-6-allyl-7-hydroxycoumarin (3, R=CN, R'=H) (0.656 g, 2.570 mmoles) in 15 mL of chloroform, at room temperature and under an inert atmosphere, was slowly added bromine (0.14 mL, 2.70 mmoles) dissolved in 15 mL of chloroform. After the addition was complete, the reaction mixture was stirred for 4 hours, then chilled in ice. The resulting precipitate was collected by suction filtration, washed with cold chloroform and dried in vacuo yielding 0.977 g (92% yield) of 3-cyano-4,8-dimethyl-6-(2,3-dibromopropyl)-7-hydroxycoumarin (4, R=CN, R'=H) as a pale brown solid. An analytical sample of 3-cyano-4,8-dimethyl-6-(2,3-dibromopropyl)-7-hydroxycoumarin (4, R=CN, R'=H) was obtained by recrystallisation from a mixture of benzene:methanol: mp 221–223° C.

Anal. Calcd for $C_{15}H_{13}Br_2NO_3$: C, 43.40; H, 3.16; N, 3.37. Found: C, 43.67; H, 2.92; N, 3.33. IR (nujol) 3500–3100, 2232, 1734 cm$^{-1}$; $^1$H-nmr (DMSO-d$_6$): δ 2.22 (s, 3H), 2.66 (s, 3H), 3.15 (dd, J$_1$=14.4 Hz, J$_2$=9.5 Hz, 1H), 3.47 (dd, J$_1$=14.5 Hz, J$_2$=4.5 Hz, 1H), 3.95–4.02 (m, 2H), 4.69–4.80 (m, 1H), 7.66 (s, 1H), 10.43 (s, 1H); $^{13}$C-nmr (DMSO-d$_6$): δ 8.68, 8.91, 18.16, 53.12, 53.42, 96.47, 110.79, 111.52, 114.91, 123.40, 126.55, 151.86, 157.53, 159.99, 163.58.

A mixture of 3-cyano-4,8-dimethyl-6-(2,3-dibromopropyl)-7-hydroxycoumarin (4, R=CN, R'=H) (0.593 g, 1.429 mmoles) and 5.6 g of oven-dried sodium carbonate in 50 mL of dry acetone was stirred under an inert atmosphere at room temperature for 24 hours. The carbonate salt was removed by suction filtration washed with acetone and the solvent evaporated under reduced pressure to yield a solid which was recrystallized from a mixture of benzene:methanol. Thus, 0.371 g (78% yield) of a mixture of (5, R=CN, T=Br) and its minor isomer (6, R=CN) was obtained as a pale brown solid: mp 204–206° C.

Anal. Calcd for $C_{15}H_{12}BrNO_3$: C, 53.91; H, 3.62; N, 4.19. Found: C, 54.03; H, 3.38; N, 4.05. IR (nujol) 2227, 1733 cm$^{-1}$; $^1$H-nmr (CDCl$_3$): δ 2.26 (s, 3H), 2.67 (s, 3H), 3.25 (dd, J$_1$=16.2 Hz, J$_2$=6.3 Hz, 1H), 3.45 (dd, J$_1$=15.7 Hz, J$_2$=9.3 Hz, 1H, 3.55–3.69 (m, 2H), 5.15–5.25 (m, 1H), 7.35 (s, 1H). Within the mixture of isomeric closure products generated herein, integration of their respective C$_{5'}$—H resonances in the furano isomer (5, R=CN, T=Br) and in the pyrano isomer (6, R=CN) revealed a 90:10 ratio favoring the expected 4',5'-dihydropsoralen (5, R=CN, T=Br). The $^1$H-nmr (CDCl$_3$) of that minor isomer (6, R=CN) was: δ 2.31 (s, 3H), 2.73 (s, 3H), 4.30–4.40 (m, 2H), 4.45–4.60 (m, 4H), 7.23 (s, 1H).

Example 13

Preparation of 3-Cyano-4,8-dimethyl-5'-(N-pyridiniummethyl)-4',5'-dihydropsoralen Bromide Salt (5, R=CN, T=pyridinium, bromide salt)

A solution of the above 90:10 mixture (0.142 g, 0.425 mmoles) of (5, R=CN, T=Br) and (6, R=CN) was reacted as for (5, R=H, T=pyridinium, bromide salt) using 2.5 mL of anhydrous pyridine. The resulting precipitate was collected by suction filtration, dried in vacuo, affording 0.155 g (88% yield) of the pyridinium salt (5, R=CN, T=pyridinium, bromide salt) as a pale grey solid: mp 303° C. (decomp.).

Anal. Calcd for $C_{20}H_{17}BrN_2O_3$: C, 58.13; H, 4.15; N, 6.78. Found: C, 57.74; H, 4.13; N, 6.71. IR (nujol) 3415 (broad), 2229, 1714 cm$^{-1}$; $^1$H-nmr (CD$_3$OD): δ 2.21 (s, 3H), 2.70 (s, 3H), 3.29–3.34 (m, 1H), 3.70 (dd, J$_1$=16.6 Hz, J$_2$=9.5 Hz, 1H), 4.95 (dd, J$_1$=13.8 Hz, J$_2$=9.3 Hz, 1H), 5.09 (dd, J$_1$=13.7 Hz, J$_2$=2.6 Hz, 1H), 5.43–5.55 (m, 1H), 7.69 (s, 1H), 8.21 (dd, J$_1$≈7 Hz, J$_2$≈7 Hz, 2H), 8.69 (dd, J$_1$≈8 Hz, J$_2$≈8 Hz, 1H), 9.10 (d, J=6.2 Hz, 2H).

According to this procedure one can prepare:

- 3-Cyano-4,8-dimethyl-5'-(N-4-ethylpyridiniummethyl)-4',5'-dihydropsoralen bromide salt by displacement of the requisite (5) with 4-ethylpyridine,
- 3-Cyano-4,8-dimethyl-5'-(N-quinoliniummethyl)-4',5'-dihydropsoralen bromide salt by displacement of the requisite (5) with quinoline,
- 3-Cyano-4,8-dimethyl-5'-[(N,N,N-trimethylammonium)methyl]-4',5'-dihydropsoralen bromide salt by displacement of the requisite (5) with trimethylamine (albeit a higher boiling solvent such as ethylene glycol dimethyl ether is required) and similar 4',5'-dihydro-5'-quaternary ammonium methyl psoralens.

Bromide anions in these salts may be exchanged for other anions (e.g., chloride or iodide) by ion exchange on a resin charged with the desired anion.

Example 14

Preparation of 3-Fluoro-4,8-dimethyl-5'-bromomethyl-4',5'-dihydropsoralen (5, R=F, T=Br)

A solution of 2-methylresorcinol (3.23 g, 26.02 mmoles), ethyl 2-fluoro-acetoacetate [E. B. Banks, N. J. Lawrence, A. L. Popplewell, *J. Chem. Soc., Chem. Commun*, 343 (1994)] (3.85 g, 25.99 mmoles) in 0.5 mL of 1,4-dioxane was added dropwise, at 0° C. and under an inert atmosphere, to 25 mL of concentrated sulfuric acid. The reaction mixture was stirred for 1.5 hours, while the temperature was increased to 25° C. Cold water (100 mL) was added, the reaction mixture was stirred for 15 minutes and the resulting precipitate was collected by suction filtration, dried in vacuo, affording 4.56 g (84% yield) of 3-fluoro-4,8-dimethyl-7-hydroxycoumarin as a white solid. An analytical sample was obtained by recrystallisation from methanol:water: mp 260° C. (decomp.).

Anal. Calcd for $C_{11}H_9FO_3$: C, 63.46; H, 4.36. Found: C, 63.14; H, 4.31. IR (nujol) 3400–3100, 1706 cm$^{-1}$; $^1$H-nmr (DMSO-$d_6$): δ 2.15 (s, 3H), 2.31 (d, J=2.7 Hz, 3H), 6.91 (d, J=8.7 Hz, 1H), 7.45 (d, J=8.7 Hz, 1H), 10.40 (s, 1H); EIMS m/z (rel int) 208 (M$^+$, base), 180 (29), 179 (17), 152 (22), 151 (13).

Allyl bromide (1.08 mL, 12.48 mmoles) was added to a mixture of 3-fluoro-4,8-dimethyl-7-hydroxycoumarin (1.73 g, 8.31 mmoles), ca. 5 g of potassium carbonate and 45 mL of dry acetone. The reaction mixture was stirred under an inert atmosphere at room temperature for 28 hours. During this time, excess allyl bromide (1.44 mL, 16.64 mmoles) was added in two portions. The carbonate salt was removed by suction filtration washed with acetone and the solvent evaporated under reduced pressure yielding a solid, which was purified by recrystallisation from a mixture of methanol:water. Thus, 1.60 g (78% yield) of 3-fluoro-4,8-dimethyl-7-allyloxycoumarin was obtained as a white solid: mp 117° C.

Anal. Calcd for $C_{14}H_{13}FO_3$: C, 67.73; H, 5.28. Found: C, 67.47; H, 5.26. IR (nujol) 1718 cm$^{-1}$; $^1$H-nmr (CDCl$_3$): δ 2.32 (s, 3H), 2.34 (d, J=2.7 Hz, 3H), 4.61 (d, J=4.9 Hz, 2H), 5.30 (d, J=10.5 Hz, 1H), 5.42 (dd, $J_1$=17.3 Hz, $J_2$=1.2 Hz, 1H), 5.97–6.13 (m, 1H), 6.86 (d, J=8.8 Hz, 1H), 7.33 (d, J=8.8 Hz, 1H); EIMS m/z (rel int) 248 (M$^+$, base), 208 (30), 207 (79), 179 (56), 41 (63), 39 (25).

A solution of 3-fluoro-4,8-dimethyl-7-allyloxycoumarin (1.56 g, 6.28 mmoles) in 20 mL of N,N-diethylaniline was deoxygenated with argon for 30 minutes and then was heated at reflux for 4 hours, while being purged by bubbling argon through the solution. The reaction mixture was chilled in ice, the resulting precipitate was collected by suction filtration and dried in vacuo. Recrystallisation from a mixture of methanol:water gave 0.859 g (55% yield) of 3-fluoro-4,8-dimethyl-6-allyl-7-hydroxycoumarin (3, R=F, R'=H) as a white solid: mp 163–164° C.

Anal. Calcd for $C_{14}H_{13}FO_3$: C, 67.73; H, 5.28. Found: C, 67.57; H, 5.21. IR (nujol) 3500–3100, 1724 cm$^{-1}$; $^1$H-nmr (CDCl$_3$): δ 2.31 (s, 3H), 2.35 (d, J=2.8 Hz, 3H), 3.47 (d, J=6.1 Hz, 2H), 5.18–5.27 (m, 2H), 5.47 (s, 1H), 5.95–6.10 (m, 1H), 7.14 (s, 1H); EIMS m/z (rel int) 248 (M$^+$, base), 233 (18), 205 (18), 177 (21), 27 (19).

3-Fluoro-4,8-dimethyl-6-allyl-7-hydroxycoumarin (3, R=F, R'=H) (0.211 g, 0.850 mmoles) was dissolved in 6 mL of chloroform. To this stirred solution, at room temperature and under an inert atmosphere, was slowly added bromine (0.046 mL, 0.89 mmoles) dissolved in 4 mL of chloroform. After the addition was complete, the reaction mixture was stirred for 16 hours, and the solvent removed under reduced pressure. Recrystallisation from a mixture of methanol:water gave 0.295 g (85% yield) of 3-fluoro-4,8-dimethyl-6-(2,3-dibromopropyl)-7-hydroxycoumarin (4, R=F, R'=H) as a white solid: mp 175–176° C.

Anal. Calcd for $C_{14}H_{13}Br_2FO_3$: C, 41.21; H, 3.21. Found: C, 41.06; H, 2.97. IR (nujol) 3500–3100, 1717 cm$^{-1}$; $^1$H-nmr (DMSO-$d_6$): δ 2.23 (s, 3H), 2.33 (d, J=2.5 Hz, 3H), 3.15 (dd, $J_1$=14.3 Hz, $J_2$=8.0 Hz, 1H), 3.46 (dd, $J_1$=14.4 Hz, $J_2$=4.9 Hz, 1H), 3.96 (d, J=5.2 Hz, 2H), 4.69–4.78 (m, 1H), 7.42 (s, 1H), 9.65 (s, 1H).

A mixture of 3-fluoro-4,8-dimethyl-6-(2,3-dibromopropyl)-7-hydroxycoumarin (4, R=F, R'=H) (0.231 g, 0.566 mmoles) and 2.2 g of oven-dried sodium carbonate in 15 mL of dry acetone was stirred under an inert atmosphere at room temperature for 16 hours. The carbonate salt was removed by suction filtration, washed with acetone and the solvent evaporated to yield a solid which was recrystallized from a mixture of methanol:water giving 0.145 g (78% yield) of a mixture of (5, R=F, T=Br) and its minor isomer (6, R=F) as a white solid: mp 143–144° C.

Anal. Calcd for $C_{14}H_{12}BrFO_3$: C, 51.40; H, 3.70. Found: C, 51.23; H, 3.38. IR (nujol) 1717 cm$^{-1}$; $^1$H-nmr (CDCl$_3$): δ 2.25 (s, 3H), 2.34 (d, J=2.9 Hz, 3H), 3.22 (dd, $J_1$=16.0 Hz, $J_2$=6.4 Hz, 1H), 3.45 (dd, $J_1$=16.0 Hz, $J_2$=9.2 Hz, 1H), 3.55 (dd, $J_1$=10.6 Hz, $J_2$=6.7 Hz, 1H), 3.63 (dd, $J_1$=10.6 Hz, $J_2$=4.5 Hz, 1H), 5.06–5.15 (m 1H), 7.18 (s, 1H). Within the mixture of isomeric closure products generated herein, integration of their respective $C_{5'}$—H resonances in the furano isomer (5, R=F, T=Br) and in the pyrano isomer (6, R=F) revealed a 89:11 ratio favoring the expected 4',5'-dihydropsoralen (5, R=F, T=Br). The $^1$H-nmr (CDCl$_3$) of that minor isomer (6, R=F) was: δ 2.25 (s, 3H), 2.34 (s, 3H), 4.15–4.25 (m, 2H), 4.25–4.50 (m, 4H), 7.04 (s, 1H).

Example 15

Preparation of 3-Fluoro-4,8-dimethyl-5'-(N-pyridiniummethyl)-4',5'-dihydropsoralen Bromide Salt (5, R=F, T=pyridinium, Bromide Salt)

A solution of the above 89:11 mixture (0.100 g, 0.306 mmoles) of (5, R=F, T=Br) and (6, R=F) was reacted as for (5, R=H, T=pyridinium, bromide salt) using 2 mL of anhydrous pyridine. The resulting precipitate was collected by suction filtration and dried in vacuo, affording 0.091 g (73% yield) of the pyridinium salt (5, R=F, T=pyridinium, bromide salt) as a white solid: mp 289° C. (decomp.).

Anal. Calcd for $C_{19}H_{17}BrFNO_3$: C, 56.17; H, 4.22; N, 3.45. Found: C, 55.82; H, 3.93; N, 3.38. IR (nujol) 3490 (broad), 1717 cm$^{-1}$; $^1$H-nmr (CD$_3$OD): δ 2.21 (s, 3H), 2.38 (d, J=2.9 Hz, 3H), 3.25–3.30 (m, 1H), 3.67 (dd, $J_1$=16.2 Hz, $J_2$=9.3 Hz, 1H), 4.78–4.92 (m, 1H), 5.09 (dd, $J_1$=13.8 Hz, $J_2$=2.6 Hz, 1H), 5.35–5.46 (m, 1H), 7.48 (s, 1H), 8.19 (dd, $J_1$≈7 Hz, $J_1$≈7 Hz, 2H), 8.68 (dd, $J_1$≈8 Hz, $J_2$≈8 Hz, 1H), 9.08 (d, J=6.2 Hz, 2H).

According to this procedure one can prepare:

3-Fluoro-4,8-dimethyl-5'-(N-4-ethylpyridiniunmethyl)-4',5'-dihydropsoralen bromide salt by displacement of the requisite (5) with 4-ethylpyridine, 3-Fluoro-4,8-dimethyl-5'-(N-quinoliniummethyl)-4',5'-dihydropsoralen bromide salt by displacement of the requisite (5) with quinoline, 3-Fluoro-4,8-dimethyl-5'-[(N,N,N-trimethylammonium)methyl]-4',5'-dihydropsoralen iodide salt by displacement of the requisite (5) with trimethylamine (albeit a higher boiling solvent such as ethylene glycol dimethyl ether is required) and similar 4',5'-dihydro-5'-quaternary ammonium methyl psoralens.

Bromide anions in these salts may-be exchanged for other anions (e.g., chloride or iodide) by ion exchange on a resin charged with the desired anion.

Example 16

Preparation of 3-Fluoro-4,8-dimethyl-5'-iodomethyl-4',5'-dihydrofurocoumarin (5, R=F, T=I)

Stirred at room temperature for three hours was 3-fluoro-4,8-dimethyl-6-allyl-7-hydroxycoumarin (3, R=F) (200 mg, 0.804 mmoles) with N-iodosuccinimide (271 mg, 1.20 mmoles) in enough methylene chloride to dissolve. Sodium bisulfite was added to decolorize before transferring to a separatory flask for washing with two 1.5 mL portions of water. Recovered was 277 mg crystals (91% yield). Further purification was achieved by chromatographing on silica gel with 30% ethyl acetate and 70% hexane.

Anal. Calcd for $C_{14}H_{12}FIO_3$: C, 44.94; H, 3.23. Found: C, 45.05; H, 3.26. $^1$H-nmr (CDCl$_3$): (2.30, (s, 3H), 2.56, (s, 3H), 3.16 (dd, $J_1$=15.9 Hz, $J_2$=6.7 Hz, 1H), 3.40 (dd, $J_1$9.3 Hz, $J_2$=7.6 Hz, 1H), 3.47 (dd, $J_1$=15.9 Hz, $J_2$=6.7 Hz, 1H), 3.51 (dd, $J_1$9.3 Hz, $J_2$=4.9, 1H), 4.98 (m, 1H), 7.28 (s, 1H).

$^{13}$C-nmr (CDCl$_3$): (8.94, 9.03, (10.73, 10.79), 36.27, 82.95, 108.62, 113.46, (117.60, 117.70), 123.48, (131.93, 132.13), (140.54, 144.47), 150.05, 155.73, 160.56.

Example 17
Preparation of 3-fluoro-4,8-dimethyl-5'-acetomercurimethyl-4',5'-dihydrofulrocoumarin 5 (R=F, T=HgOAc)

At room temperature in enough ethanol to solubilize, was added 3-fluoro-4,8-dimethyl-6-allyl-7-hydroxycoumarin 3 (R=F, R'=H) (50 mg, 0.20 mmoles) with the dropwise addition of a solution of mercury acetate (64 mg, 0.20 mmoles) in ethanol. Crystals, 92 mg, (92% yield) were recovered by filtration and washed with water.

Anal. Calcd for C$_{16}$H$_{17}$FHgO$_5$: C, 37.76; H, 3.37. Found: C, 37.66; H, 2.78. $^1$H-nmr (DMSO-d$_6$): δ 1.84 (s, 3H), 2.10 (s, 3H), 2.35 (s, 3H), 2.49 (t, J=2.5 Hz, 2H), 2.93 (dd, J$_1$=16 Hz, J$_2$=8 Hz, 1H), 3.43 (dd, J$_1$=16 Hz, J$_2$=8 Hz, 1H), 5.31 (m, 1H), 7.40 (s, 1H).

Example 18
Preparation of 4,8-Dimethyl-5'-iodomethyl-4',5'-dihydropsoralen (5, R=H, T=I)

Route One—To 50 mL methylene chloride was added compound 4,8-dimethyl-allyl-7-hydroxycoumarin (3, R=H, R'=H) (2.00 g, 8.68 mmoles) with stirring to dissolve the solid before the addition of N-iodosuccinimide (NIS) (2.92 g, 13.0 mmoles). The reaction mixture was stirred at room temperature overnight. The GC/MS indicated conversion was complete. Saturated bisulfite was added with stirring continuing for ten minutes. The THF was evaporated, solids were taken up in chloroform, washed with a saturated NaCl solution, washed with water and dried over MgSO$_4$. Evaporation of the solvent gave 2.84 g (92% yield). Recrystallization from ethanol gave white crystals with a mp of 137.4–138.2° C. TLC with 5% MeOH/95% CHCl$_3$ showed one spot with Rf 0.78.

Anal. Calcd for C$_{14}$H$_{13}$IO$_3$: C, 47.21; H, 3.68. Found: C, 48.02; H, 3.82. $^1$H-nmr (CDCl$_3$): (2.19 (s, 3H), 2.28 (s, 3H), 3.04 (dd, J$_1$=15.8 Hz, J$_2$=6.7 Hz, 1H), 3.33 (dd, J$_1$=9.9 Hz, J$_2$=7.6, 1H), 3.40 (dd, J$_1$=15.8 Hz, J$_2$=6.7, 1H), 3.44 (dd, J$_1$=9.9, J$_2$=4.9), 4.88 (m, 1H), 6.01 (s, 1H), 7.13 (s, 1H). $^{13}$C-nmr (CDCl$_3$): (8.48, 8.61, 19.04, 35.77, 82.56, 108.13, 111.24, 113.99, 117.35, 121.98, 152.81, 153.19, 160.91, 161.56.

Route Two—To 50 mL of methylene chloride was added compound 4,8-dimethyl-6-allyl-7-hydroxycoumarin (3, R=H, R'=H) (5.02 g, 21.8 mmoles), 12 mL 1 M SnCl$_4$ and I$_2$ (5.50 g, 22.6 mmoles). Stirring was continued at room temperature overnight. Ice water was added and mixture was treated with 0.5 N NaOH, washed with 5% Na$_2$S$_2$O$_4$ and water before drying over MgSO$_4$. Methylene chloride was removed in vacuo with a yield of 6.37 g (82%). Recrystallization from ethanol or purification on a silica column with 1% acetone/99% methylene chloride afforded pure product.

Example 19
Preparation of 3-Iodo-4,8-dimethyl-5'-iodomethyl-4',5'-dihydropsoralen (5, R=I, T=I)

To one mL of glacial acetic acid was added 4,8-dimethyl-5'-iodomethyl-4',5'-dihydropsoralen (5, R=H, T=I) (100 mg, 28 mmoles) and ICl (72 mg, 42 mmoles) with heating at 50° C. and stirring continued overnight. TLC of reaction mixture on silica gel with 5% MeOH/95% CHCl$_3$ showed three spots with Rfs of 0.81, 0.57 and 0.27. Tan crystals were collected by filtration and washed with ether. The yield was 114 mg (85%) after recrystallization from ethanol. Purification on silica column using 5% MeOH/95% CHCl$_3$, afforded white crystals with mp 213–214° C.

Anal. Calcd for C$_{14}$H$_{12}$I$_2$O$_3$: C, 34.88; H, 2.51. Found: C, 35.09; H, 2.61. $^1$H-nmr :CDCl$_3$): (2.29 (s, 3H), 2.65 (s, 3H), 3.14 (dd, J$_1$=15.8 Hz, J$_2$=6.7 Hz, 1H), 3.38 (m, 3H), 4.95 (m, 1H), 7.31 (s, 1H). $^{13}$C-nmr (CDCl$_3$): (8.52, 8.61, 25.81, 35.75, 82.79, 88.14, 107.85, 113.61, 117.86, 118.10, 152.25, 156.58, 158.25, 161.21.

Example 20
Preparation of 4,8-Dimethyl-5'-morpholinomethyl-4',5'-dihydropsoralen (5, R=H, T=morpholino)

4,8-Dimethyl-5'-iodomethyl-4',5'-dihydropsoralen (5, R=H, (500 mg, 1.40 mmoles) was added to dry morpholine (4 mL) and heated at reflux for three hours. The mixture was evaporated in vacuo to remove excess morpholine and the product was taken up in methylene chloride and washed with water. The organic layer was dried and evaporated in vacuo to recover tan crystals, 0.306 g (70% yield). The product was purified by column chromatography on silica gel with 30% ethyl acetate/70% hexane to give white crystals with mp 159.8–160.9° C. A second portion was purified on a silica column with 5% MeOH/95% chloroform with an Rf 0.43. This fraction was submitted for elemental analysis.

Anal. Calcd for C$_{18}$H$_{21}$NO$_4$: C, 68.55; H, 6.71; N, 4.44. Found: C, 68.38; H, 6.73; N, 4.34. $^1$H-nmr (CDCl$_3$): (2.17 (s, 3H), 2.27 (s, 3H), 2.40–2.70 (m, 6H), 2.99 (dd, 1H), 3.25 (dd, J$_1$=15.3 Hz, J$_2$=9.2 Hz, 1H), 3.63 (t, J=4.8 Hz, 4H), 4.92 (m, 1H), 5.98 (s, 1H), 7.13 (s, 1H). $^{13}$C-nmr (CDCl$_3$): (8.49, 19.00, 33.60, 54.34 (2 carbons), 62.87, 66.93 (2 carbons), 82.83, 107.66, 110.90, 113.53, 117.23, 122.64, 152.80, 153.05, 160.72, 161.61.

Example 21
Preparation of 4,8-Dimethyl-5'-[N,N-β-(hydroxyethylamino)-methyl]-4',5'-dihydropsoralen (5, R=H, T=N,N-Bis-hydroxyethylamino)

4,8-dimethyl-5'-iodomethyl-4',5'-dihydropsoralen (5, R=H, T=I) (500 mg, 1.4 mmoles) was added to 3 mL diethanolamine and heated at 80° C. for four hours. Recovery of pure product was difficult because of the high boiling point of diethanolamine. Purified by column chromatography using 30% hexanes/70% ethyl acetate, recovered glassy brown crystals weighed 0.243 g (52% yield). Recrystallization from ethanol/ether gave glassy brown crystals with a broad melting point (81% pure).

Anal. Calcd for C$_{18}$H$_{23}$NO$_5$: C, 64.85; H, 6.95; N, 4.20. Found: C, 63.67; H, 6.91; N, 4.22. $^1$H-nmr (CD$_3$COCD$_3$): (2.19 (s, 3H), 2.40 (s, 3H), 2.79 (t, 4H), 2.91 (t, 2H), 3.08 (dd, 1H), 3.37 (dd, 2H), 3.57 (t, 4H), 5.05 (m, 1H), 6.04 (s, 1H), 7.40 (s, 1H). $^{13}$C-nmr (CDCl$_3$): (8.74, 19.30, 33.38, 57.64 (2 carbons), 59.98, 60.16 (2 carbons), 83.62, 108.15, 111.07, 114.02, 117.81, 123.13, 153.29, 153.54, 161.21, 162.10.

Example 22
Preparation of 4,8-Dimethyl-5'-(2,6-dimethylmorpholino) methyl-4',5'-dihydropsoralen (5, R=H, T=2,6-dimethylmorpholino)

4,8-Dimethyl-5'-iodomethyl-4',5'-dihydropsoralen (5, R=H, T=I) (250 mg, 0.700 mmoles) was added to 2 mL 2,6-dimethylmorpholine and heated at close to reflux overnight. Excess dimethylmorpholine was removed under vacuum. Crystals recovered weighed 0.142 g (73.6% yield). TLC using 5% MeOH/95% CHCL$_3$ showed two spots with Rf 0.82 and 0.46. Purification on silica gel column using the same solvent afforded white crystals with mp 167.2–169.0° C.

Anal. Calcd for C$_{20}$H$_{25}$NO$_4$×0.11 H$_2$O: C, 69.51; H, 7.30; N, 4.05. Found: C, 69.51; H, 7.46; N, 3.87. $^{13}$C-nmr (DMSO-d$_6$): (8.27, 18.55, 18.96 (2 carbons), 32.88, 59.30, 59.71, 61.78, 70.94 (2 carbons), 82.46, 105.99, 109.92, 113.03, 118.36, 123.27, 152.32, 153.90, 160.32, 160.77.

Example 23

Preparation of 4,8-Dimethyl-5'-[(N,N-dimethylamino) methyl]-4',5'-dihydropsoralen Hydroiodide Salt (5, R=H, T=dimethylaminohydro iodide salt)

4,8-Dimethyl-5'-iodomethyl-4',5'-dihydropsoralen (216 mg, 0.606 mmoles) was added to a Teflon lined metal reactor with dimethylamine (2 mL dimethylamine in methanol, 2M solution). The reactor was flushed with nitrogen then sealed before heating to 95° C. for three hours. $^{13}$C NMR indicates conversion to trimethylpsoralen mixed with the desired 4,8-dimethyl-5'-[(N,N-dimethylamino)methyl]-4',5'-dihydropsoralen (1:1). Recovered weight was 206 mg. The mixture was purified by refluxing in chloroform to solubilize the trimethylpsoralen and the 4,8-Dimethyl-5'-[(N,N-dimethylamino)methyl]- 4',5'-dihydropsoralen hydroiodide salt (5, R=H, T=dimethylaminohydro iodide salt) was collected by filtration.

Anal. Calcd for $C_{16}H_{20}NIO_3$: C, 47.90; H, 5.02; N, 3.49. Found: C, 48.27; H, 4.86; N, 3.43.

By a similar procedure one may prepare the amines or amine salts of:

4,8-dimethyl-5'-diethanolaminomethyl-4',5'-dihydropsoralen 5 (R=H, T=diethanolamino) by the displacement of the iodine by diethanolamine.

4,8-dimethyl-5'-dimethylmorpholinomethyl-4',5'-dihydropsoralen 5 (R=H, T=dimethylmorpholino) by the displacement of the iodine by dimethyl morpholine.

4,8-dimethyl-5'-dimethylaminomethyl-4',5'-dihydropsoralen hydroiodide salt 5 (R=H, T=dimethylamino hydroiodide salt) by displacement of the iodide with dimethylamine. Based on the volatility of dimethylamine, this reaction requires the use of a sealed, Teflon lined metal reactor to prevent loss of dimethylamine during heating.

Example 24

Preparation of 4,8-Dimethyl-5'-(N-pyridiniummethyl)-4',5'-dihydropsoralen Iodide Salt (5, R=H, T=pyridinium, I salt)

4,8-Dimethyl-5'-iodomethyl-4',5'-dihydropsoralen (5, R=H, R'=I) (0.200 g, 56.0 mmoles) was added to 4 mL pyridine and heated at reflux overnight. Crystals were collected by filtration and washed with ether. The yield was 0.196 g (80%). Recrystallization from methanol was required to obtain buff yellow crystals, that melted between 295–300° C.

Anal. Calcd for $C_{19}H_{18}INO_3$: C, 52.43; H, 4.17; N, 3.22. Found: C, 52.46; H, 4.31; N, 3.14. $^1$H-nmr (CD$_3$OD): (2.36 (s, 3H), 2.48 (s, 3H), 3.19 (dd, J$_1$=16.5 Hz, J$_2$=5.5 Hz 1H), 3.60 (m, 1H), 4.82 (dd, J$_1$=14 Hz, J$_2$=10.3 Hz 1H), 5.04 (d, J$_1$=12.2 Hz), 5.40 (m, 1H), 6.19 (s, 1H), 7.51 (s, 1H), 8.21 (t, J$_1$=6.1 Hz, 2H), 8.65 (t, J$_1$=8.5 Hz, 1H), 9.10 (d, J=6.1 Hz, 2H). $^{13}$C-nmr (DMSO-d$_6$): (8.36, 18.63, 31.80, 63.24, 82.10, 106.99, 110.58, 113.83, 118.70, 122.30, 128.11 (2 carbons), 145.51 (2 carbons), 146.41, 152.36, 153.90, 159.51, 160.22.

By a similar procedure, one may also prepare:

4,8-dimethyl-5'-(N,N,N-trimethylaminomethyl)-4',5'-dihydropsoralen iodide salt (5, R=H, T=trimethylammonium hydroiodide salt) from trimethyl amine.

Other appropriate quaternary ammonium salts can be synthesized from tertiary amine reactants.

Example 25

Preparation of 3-Bromo-4,8-dimethyl-5'-iodomethyl-4',5'-dihydropsoralen (5, R=Br, T=I)

Route one—To 15 mL methylene chloride was added 3-bromo-4,8-dimethyl-6-allyl-7-hydroxycoumarin (3, R=Br, R'=H) (0.200 g, 0.645 mmoles) and N-iodosuccinimide (0.217 g, 0.967 mmoles). The flask was stoppered and stirred overnight at room temperature. Bisulfite was added and stirring continued for an additional ten minutes. The methylene chloride layer was extracted with water. Unreacted starting material remaining was removed by a base extraction. The organic layer was dried over MgSO$_4$, and evaporated to give a pale mustard colored solid. The product may be recrystallized from ethanol or purified by column chromatography using 5% MeOH/95% CDCl$_3$. The yield of white crystals was 0.271 g (77%) with mp of 188.7–189.40° C.

Anal. Calcd for $C_{14}H_{12}BrIO_3$: C, 38.65; H, 2.78. Found: C, 39.39; H, 2.89. $^1$H-nmr (CDCl$_3$): (2.30, (s, 3H), 2.56, (s, 3H), 3.16 (dd, J$_1$=15.9 Hz, J$_2$=6.7 Hz, 1H), 3.40 (dd, J$_1$=9.3 Hz, J$_2$=7.6 Hz, 1H), 3.47 (dd, J$_1$=15.9 Hz, J$_2$=6.7 Hz, 1H) 3.51 (dd, J$_1$=9.3 Hz, J$_2$=4.9, 1H), 4.98 (m, 1H), 7.28 (s, 1H); $^{13}$C-nmr (CDCl$_3$): (8.52, 8.61 19.81, 35.80, 82.74, 108.03, 109.15, 113.84, 117.86, 122.89, 151.29, 151.54, 157.53, 161.06.

The 3-bromo-4,8-dimethyl-5'-iodomethyl-4',5'-dihydropsoralen may also be generated by the iodine/SnCl$_4$ ring closure of bromo-4,8-dimethyl-6-allyl-7-hydroxycoumarin.

Route 2—To 4,8-dimethyl-5'-iodomethyl-4',5'-dihydropsoralen (5, R=H, T=I) (0.075 g, 0.210 mmoles) in methylene chloride was added NBS (0.056 g, 0.310 mmoles). Stirring was continued in the dark at room temperature overnight. The solvent was evaporated in vacuo, solids were extracted with chloroform and the organic layer was washed with bisulfite and water. The organic layer was dried and solvent removed in vacuo to recover 0.076 g (84%) product. Recrystallization from ethanol afforded white crystals with mp 188.9–189.50° C.

Example 26

Preparation of 3-bromo-4,8-dimethyl-5'-morpholinomethyl-4',5'-dihydropsoralen 5, (R=Br, T=morpholino)

To 3-bromo-4,8-dimethyl-5'-iodomethyl-4',5'-dihydropsoralen 5, (R=Br, T=I) (200 mg, 0.459 mmoles) was added to morpholine (2 mL) in a vial equipped with an air condenser and the mixture was heated at reflux overnight. Excess morpholine was evaporated and product taken up in methylene chloride, washed with water and dried, before evaporation of solvent, to yield approximately 80%.

According to this procedure one can prepare the following amines or salts thereof:

3-bromo-4,8-dimethyl-5'-N,N-diethanolaminomethyl-4',5'-dihydropsoralen 5, (R=Br, T=N,N-diethanolamino) from diethanolamine.

3-bromo-4,8-dimethyl-5'-dimethylmorpholinomethyl-4',5'-dihydropsoralen 5, (R=Br, T=dimethylmorpholino) from dimethyl morpholine.

3-bromo-4,8-dimethyl-5'-N,N-dimethylaminomethyl-4',5'-dihydropsoralen iodide salt 5, (R=Br, T=dimethylamino hydroiodide salt) from dimethylamine. [This reaction requires the use of a Teflon-lined pressurized metal reactor.]

Example 27

Preparation of 3-Bromo-4,8-dimethyl-5'-(N-pyridiniummethyl)-4',5'-dihydropsoralen Iodide Salt (5, R=H, T=pyridinium, I salt)

3-Bromo-4,8-dimethyl-5'-iodomethyl-4',5'-dihydropsoralen (5, R=Br, R'=I) (0.200 g, 46.0 mmoles)

was added to 3 mL pyridine and heated at reflux overnight. Crystals were collected by filtration and washed with ether. Recrystallization from ethanol was required to obtain pure product, mustard colored crystals, which decomposed above 2700° C. The yield was 0.100 g (57%).

Anal. Calcd for $C_{19}H_{17}BrINO_3$: C, 44.34; H, 3.30; N, 2.72. Found: C, 44.39; H, 3.24; N, 2.68. $^1$H-nmr (CD$_3$OD): (2.36 (s, 3H), 2.48 (s, 3H), 3.19 (dd, J$_1$=16.5 Hz, J$_2$=5.5 Hz 1H), 3.60 (m, 1H), 4.82 (dd, J$_1$=14 Hz, J$_2$=10.3 Hz 1H), 5.04 (d, J$_1$=12.2 Hz, 1H), 5.40 (m, 1H), 7.51 (s, 1H), 8.21 (t, J$_1$=6.1 Hz, 2H), 8.65 (t, J$_1$=8.5 Hz, 1H), 9.10 (d, J=6.1 Hz, 2H).

By a similar procedure, one may also prepare 3-bromo-4,8-dimethyl-5'-N,N,N-trimethylaminomethyl-4',5'-dihydropsoralen iodide salt 5, (R=Br, T=N,N,N-trimethylamino, I salt) from trimethylamine.

Example 28
Preparation of 3-Cyano-4,8-dimethyl-5'-iodomethyl-4',5'-dihydropsoralen (5, R=CN, T=I)

3-Cyano-4,8-dimethyl-6-allyl-7-hydroxycoumarin (3, R=CN) (69.0 mg, 0.270 mmoles) was added with NIS (91.0 mg, 0.405 mmoles) in 2 mL deuterochloroform and stirred at room temperature overnight. Saturated bisulfite was added and stirring was continued for ten minutes. The organic layer was washed with water and dried over MgSO$_4$. The solvent was evaporated in vacuo. Recovered was 70.0 mg (71%) bright yellow crystals after column chromatography using 5% MeOH/95% CHCl$_3$ on silica gel. The mp was 234.7–234.9° C.

Anal. Calcd for $C_{15}H_{12}INO_3$: C, 47.21; H, 3.17; N, 3.67. Found: C, 47.08; H, 3.29. $^1$H-nmr (CDCl$_3$): 2.28 (s, 3H), 2.70 (s, 3H), 3.16 (dd, J$_1$(15 Hz, J$_2$(6 Hz, 1H), 3.39 (m, 3H), 5.04 (m, 1H), 7.36 (s, 1H). $^{13}$C-nmr (CDCl$_3$): (8.44, 8.60, 18.50, 35.69, 83.42, 96.52, 108.89, 112.67, 114.53, 119.17, 121.98, 153.65, 157.83, 162.25, 164.14.

Example 29
Preparation of 3-cyano-4,8-dimethyl-5'-acetomercurimethyl-4',5'-dihydrofurocoumarin 5 (R=CN, T=HgOAc)

3-Cyano-4,8-dimethyl-6-allyl-7-hydroxycoumarin 3 (R=CN, R'=H) (0.100 g, 0.391 mmoles) was dissolved in 15 mL ethanol with slight heating. After addition of Hg(OAc)$_2$ (0.142g, 0.442 mmoles) in 2 mL ethanol, within two minutes, a precipitation formed. Heating and stirring continued for two hours. The first crop of crystals recovered weighed 160 mg (80% Yield).

$^1$H-nmr (DMSO-d$_6$): δ 1.85 (s, 3H), 2.12 (s, 3H), 2.48 (s, 3H), 2.64 (t, J=2.5 Hz, 2H), 2.94 (dd, J$_1$=16.5 Hz, J$_2$=6.7 Hz, 1H), 3.47 (dd, J$_1$=16.5 Hz, J$_2$=6.7 Hz, 1H), 5.32 (m, 1H), 7.67 (s, 1H).

Example 30
Preparation of 3-Cyano-4,8-dimethyl-5'-(N-pyridiniummethyl)-4',5'-dihydropsoralen Iodide Salt (5, R=CN, T=pyridinium, I salt)

Pyridine (3 mL) was added with 3-cyano-4,8-dimethyl-5'-iodomethyl-4',5'-dihydropsoralen (175 mg, 0.458 mmoles) and heated at reflux for five hours. Crystals were collected by filtration and washed with ether. Recrystallization from ethanol gave pale orange crystals which melted above 300° C. Yield was 168 mg (78%) purified product.

Anal. Calcd for $C_{20}H_{17}IN_2O_3 \times 1.2$ H$_2$O: C, 49.75; H, 4.24; N, 5.81. Found: C, 49.75; H, 4.15; N, 5.68. $^1$H-nmr (CD$_3$OD): (2.21 (s, 3H), 2.70 (s, 3H), 3.29–3.34 (m, 1H), 3.70 (dd, J$_1$=16.3 Hz and J$_2$=9.3 Hz, 1H), 4.95 (m, 1H), 5.09 (dd, J$_1$=13.7 Hz and J$_2$=2.6 Hz, 1H), 5.50 (m, 1H), 7.69 (s, 1H), 8.21 (dd, J$_1$=7 Hz and J$_2$=7 Hz), 8.69 (dd, 7 Hz, 1H) 9.10 (d, 5.5 Hz, 2H). $^{13}$C-nmr (DMSO-d$_6$): (8.19, 18.47, 31.43, 63.08, 83.01, 96.52, 107.33, 112.49, 114.79, 120.70, 124.07, 128.09 (2 carbons), 145.41 (2 carbons), 146.40, 152.65, 157.36, 162.43, 163.70.

Example 31
Preparation of 4,8-Dimethyl-5'-acetomercurimethyl-4',5'-dihydropsoralen (5, R=H, T=HgOAc)

4,8-Dimethyl-6-allyl-7-hydroxycoumarin (3, R=H, R'=H) (230 mg, 1.00 mmole) was added to 25 mL methanol and heated to dissolve. Mercury acetate (318 mg, 1.00 mmole) was dissolved in 1 mL water prior to dropwise addition over five minutes into the Claisen/methanol mixture. This was heated slightly for three hours with stirring. After cooling, the crystals were collected by filtration. The crystals were taken up into methylene chloride, extracted with water, then dried with magnesium sulfate. Evaporating in vacuo recovered 446 mg (91% yield). Recrystallization from methanol/ether afforded white crystals with mp 194.9–195.5° C.

Anal. Calcd for $C_{16}H_{16}HgO_5$: C, 39.32; H, 3.30. Found: C, 39.26; H, 3.08. $^1$H-nmr (DMSO-d$_6$): (1.84 (s, 3H), 2.10 (s, 3H), 2.35 (s, 3H), 2.49 (t, J=2.5 Hz, 2H), 2.93 (dd, J$_1$=16 Hz, J$_2$=8 Hz, 1H),3.43(dd, J$_1$=16Hz, J$_2$=8 Hz, 1H), 5.31 (m, 1H),6.12(s, 1H), 7.40 (s, 1H). $^{13}$C-nmr (DMSO-d$_6$): (9.60, 18.55, 23.61, 29.26, 37.60, 85.38, 105.95, 109.74, 112.83, 118.30, 123.81, 152.51, 153.91, 160.35, 160.81, 174.68.

Example 32
Preparation of 4,8-Dimethyl-5'-chloromercurimethyl-4',5'-dihydropsoralen (5, R=H, T=HgCl)

4,8-Dimethyl-6-allyl-7-hydroxycoumarin (3, R=H, R'=H) (0.750g, 3.26 mmoles) was dissolved in 10 mL ethanol with slight heating. Over a five minute period, to this solution was added a solution of HgCl$_2$ (0.991 g, 3.73 mmoles) dissolved in 1 mL ethanol. This was heated at reflux for one hour. The product was recovered as the ring closed product. The yield was 1.09 g (72%). The crystals were taken up in hot ethanol and refluxed for several minutes before cooling. The white crystals were recovered by filtration and washed with ether. The product decomposed between 245–255° C.

Anal. Calcd for $C_{14}H_{13}ClHgO_3$: C, 36.15; H, 2.82. Found: C, 36.39; H, 2.69. $^1$H-nmr (DMSO-d$_6$): (2.10 (s, 3H), 2.26 (s, 3H), 2.49 (t, J=2.5 Hz, 2H), 2.92 (dd, J$_1$=16 Hz, J$_2$=8 Hz, 1H), 3.43 (dd, J$_1$=16 Hz, J$_2$=8 Hz, 1H), 5.31 (m, 1H), 6.13 (s, 1H), 7.42 (s, 1H). $^{13}$C-nmr (DMSO-d$_6$): (8.35, 18.50, 29.61, 37.47, 85.31, 105.96, 109.74, 112.86, 118.37, 123.86, 153.91, 160.15, 160.81, 161.30.

Example 33
Preparation of 4,8-Dimethyl-5'-iodomercurimethyl-4',5'-dihydropsoralen (5, R=H, T=HgI)

4,8-Dimethyl-5'-acetomercurimethyl-4',5'-dihydropsoralen (3, R=H, T=HgOAc) (130 mg, 266 mmoles) was dissolved in 75 mL ethanol and treated, by heating, with potassium iodide (145 mg, 880 mmoles) in water. The mixture was heated at reflux for 1.5 hour. Crystals were filtered and washed with water. The yield was nearly quantitative. White crystals were recrystallized from ethanol with mp 137.3–138.2° C.

Anal. Calcd for $C_{14}H_{13}HgIO_3$: C, 30.21; H, 2.35; Hg, 36.02; I, 22.80. Found: C, 32.41; H, 2.52; Hg, 33.58; I, 22.56. $^1$H-nmr (DMSO-d$_6$): (2.10 (s, 3H), 2.34 (s, 3H), 2.34 (s, 3H), 2.48 (t, 2H), 2.90 (dd, 1H), 3.40 (dd, 1H), 5.40 (m, 1H), 6.10 (s, 1H), 7.40 (s, 1H). $^{13}$C-nmr (DMSO-d$_6$): (8.60, 18.55, 23.56, 37.58, 85.38, 105.94, 109.70, 112.83, 118.33, 123.80, 151.90, 153.92, 160.34, 160.81.

Example 34
Preparation of 4,8-dimethyl-5'-trifluoroacetomercurimethyl-4',5'-dihydropsoralen (5, R=H, T=HgOCOCF$_3$)

4,8-Dimethyl-6-allyl-7-hydroxycoumarin (3, R=H, R'=H) (230 mg, 1.00 mmole) was added to 25 mL methanol and dissolved by heating. Mercuric trifluoroacetate (443 mg, 1.04 mmoles) in ethanol was added dropwise with stirring. The product was recovered by filtration. The yield was nearly quantitative and white crystals were purified by ethanol/ether recrystallization. Decomposition of crystals began at 185° C.

Anal. Calcd for $C_{16}H_{13}F_3HgO_5 \times 1.2\ H_2O$: C, 34.02; H, 2.76; Hg, 35.48. Found: 34.02; H, 2.53; Hg, 35.53. $^1$H-nmr (DMSO-d$_6$): (2.19 (s, 3H), 2.35 (s, 3H), 2.49 (t, 2H), 2.75 (dd, 1H), 2.85 (dd, 1H), 3.30 (dd, 1H), 5.31 (m, 1H), 6.10 (s, 1H), 7.37 (s, 1H).

Example 35
Preparation of 3-Fluoro-4,8-dimethyl-5'-acetomercurimethyl-4',5'-dihydropsoralen (5, R=F, T=HaOAc)

Using sufficient ethanol to form a solution, there was added 3-fluoro-4,8-dimethyl-6-allyl-7-hydroxycoumarin (3, R=F) (50.0 mg, 0.20 mmoles) followed by the dropwise addition of a solution of mercury acetate (64.0 mg, 0.20 mmoles) in 3 mL ethanol. Crystals, 92.0 mg (92% yield), were recovered by filtration and washed with water. Recrystallization from methanol gave white crystals with mp 218–219° C.

Anal. Calcd for $C_{16}H_{17}FHgO_5$: C, 37.76; H, 3.37. Found: C, 37.66; H, 2.75. $^1$H-nmr (DMSO-d$_6$): (1.84 (s, 3H), 2.10 (s, 3H), 2.35 (s, 3H), 2.49 (t, J=2.5 Hz, 2H), 2.93 (dd, J$_1$=16 Hz, J$_2$=8 Hz, 1H), 3.43 (dd, J$_1$=16 Hz, J$_2$=8 Hz, 1H), 5.31 (m, 1H), 7.40 (s, 1H).

Example 36
Preparation of 3-Cyano-4,8-dimethyl-5'-acetomercurimethyl-4',5'-dihydropsoralen (5 R=CN, T=HgOAc)

3-Cyano-4,8-dimethyl-6-allyl-7-hydroxycoumarin (3, R=CN, R'=H) (0.100 g, 0.391 mmoles) was dissolved in 15 mL ethanol with slight heating. After addition of Hg(OAc)$_2$ (0.142 g, 0.442 mmoles) in 2 mL ethanol, within two minutes, a precipitation formed. Heating and stirring continued for two hours. The first crop of crystals recovered weighed 160 mg (80% yield). Methanol was employed to recrystallize pale yellow crystals with mp 214–215° C.

Anal. Calcd for $C_{17}H_{17}HgNO_5$: C, 39.58; H, 3.32; Hg, 38.87; N; 2.72. Found: C, 41.04; H, 3.00; Hg, 39.16; N, 3.76. $^1$H-nmr (DMSO-d$_6$): (1.85 (s, 3H), 2.12 (s, 3H), 2.48 (s, 3H), 2.64 (t, J=2.5 Hz, 2H), 2.94 (dd, J$_1$=16.5 Hz, J$_2$=6.7 Hz, 1H), 3.47 (dd, J$_1$=16.5 Hz, J$_2$=6.7 Hz, 1H), 5.32 (m, 1H), 7.67 (s, 1H).

Example 37
Preparation of 4,8-Dimethyl-5'-iodomethyl-4',5'-dihydropsoralen (5, R=H, T=I)

4,8-Dimethyl-5'-iodomercurimethyl-4',5'-dihydropsoralen (5, R=H, T=HgI) (2.60 g, 4.60 mmoles) was finely ground and added to iodine (0.655 g, 2.60 mmoles) and potassium iodide (1.196 g, 7.20 mmoles) in 75 mL water. The mixture was heated to reflux, when heating of the dark red solution was discontinued. Upon evaporation in vacuo red oil resulted which hardened on standing. This was recrystallized from ethanol to give a low yield of pale pink crystals. A second recrystallization afforded white crystals that had physical and spectral properties in agreement with those of the previous synthesis.

Example 38
Preparation of 2-Chloromercurimethyl-2,3-dihydrobenzofuran

Mercury chloride (1.31 g, 4.82 mmoles) was added to 50 mL water before the addition of allyl phenol (0.625 g, 4.65 mmoles) was accomplished dropwise. A precipitate formed immediately. The product was recovered by filtration and washed with water to give 1.49 g (89% yield). Recrystallization from ethanol afforded white crystals with mp 136.1–136.3° C.

Anal. Calcd for $C_9H_9HgClO$: C, 29.29; H, 2.46; Hg, 54.32. Found: C, 29.62; H, 2.40; Hg, 55.48. $^1$H-nmr (DMSO-d$_6$): (2.09 (d, J=2.5 Hz, 2H), 2.83 (dd, J$_1$=16 Hz, J$_2$=8 Hz, 1H), 3.25 (dd, J$_1$=16 Hz, J$_2$=8 Hz, 1H), 5.15 (m, 1H), 6.72 (m, 2H), 7.06 (m, 2H). $^{13}$C-nmr (CDCL$_3$): (32.39, 39.33, 82.26, 110.33, 121.24, 125.79, 126.68, 128.80, 177.75.

Example 39
Preparation of 2-Acetomercurimethyl-2,3-dihydrobenzofuran

Mercuric acetate (2.37 g, 7.43 mmoles) was dissolved in 10 mL water and added dropwise with stirring to the o-allylphenol mixture (a suspension of 1.00 g allyl phenol (7.45 mmoles) in 10 mL water). The product was recovered by filtration, with first crop providing 1.76 g (60% yield) and second crop providing 0.88 g (30%). White crystals were recrystallized from ethanol with mp 80–81° C.

Anal. Calcd for $C_{11}H_{12}HgO_3$: C, 33.64; H, 3.08; Hg, 51.06. Found: C, 33.43; H, 2.89; Hg, 52.88. $^1$H-nmr(DMSO-d$_6$): (1.84 (s, 3H), 2.09 (d, J=2.5 Hz, 2H), 2.83 (dd, J$_1$=16 Hz, J$_2$=7 Hz, 1H), 3.29 (dd, J$_1$=16 Hz, J$_2$=8 Hz, 1H), 5.05 (m, 1H), 6.72 (m,2H), 7.02 (m, 2H). $^{13}$C-nmr (CDCL$_3$): (23.83, 32.39, 39.33, 82.26, 110.33, 121.24, 125.79, 126.68, 128.80, 158.83, 177.75.

Example 40
Preparation of 2-Iodomercurimethyl-2,3-dihydrobenzofuran

The 2-acetomercurimethyl-2,3-dihydrobenzofuran (0.300 g, 0.763 mmoles) was taken up in 20 mL water with heating to bring about solution. Potassium iodide (0.415 g, 2.50 mmoles) was added to the reaction mixture. Heating was continued for two hours and the product was recovered by filtration and recrystallized from ethanol, to yield 0.175 g (50% yield). The mp was 115.8–117.2° C.

Anal. Calcd for $C_9H_9HgIO$: Hg, 43.53; I; 27.55. Found: Hg, 43.84; I, 27.32. $^1$H-nmr (CDCL$_3$) (2.21 (dd, J$_1$=11.9 Hz, J$_2$=4.6 Hz, 1H), 2.40 (dd, J$_1$=11.6 Hz, J$_2$=5.5 Hz, 1H), 2.75 (dd, J$_1$=15.9 Hz, J$_2$=5.5 Hz, 1H), 3.38 (dd, J$_1$=15.9 Hz, J$_2$=8.5 Hz, 1H), 5.48 (m, J$_1$=8.5 Hz, J$_2$=5.5 Hz, 1H), 6.84 (m, 2H), 7.16 (m, 2H). $^{13}$C-nmr (DMSO-d$_6$): (39.17, 47.04, 82.80, 110.74, 121.61, 125.93, 126.50, 129.18, 158.83.

Example 41
Pharmacological Assay

Representative examples of the compounds described and claimed herein were tested in this assay for biological activity and found to be potent inhibitors of cell growth. Inhibition of cell growth was rapid, dependent on concentration, and required light activation. These findings directly demonstrate that the newly synthesized compounds are potential phototherapeutics for human proliferative diseases. A description of this assay follows.

The photobiological activity was assayed using a keratinocyte cell line grown in a monolayer culture. In this assay, PAM 212 keratinocytes were grown in Dulbecco's Modified Eagle's medium supplemented with 10% newborn calf serum in a 5% carbon dioxide incubator. Cells were inoculated into 6-well Falcon plastic culture dishes at 25,000 cells per well. After 24 hours, the medium was charged to fresh growth medium supplemented with increasing concentrations of the test compounds or the control medium. Controls and test concentrations were analyzed in triplicate.

These plates were then incubated in a 37 degree C. carbon dioxide incubator. After 30 minutes culture plates were exposed to UVA light (UVA, 320–400 nm) emitted from a bank of four BLB fluorescent light tubes (F40 BL, Sylvania) placed approximately 10 cm above the cell culture plates. The incident light on the culture plates was 2.4 mW/cm$^2$ as measured with an International Light UV radiometer, Model IL 442A. The cells were exposed to 1.28 J/square centimeter of UVA.

After completion of the irradiation phase, the cell culture medium was drained, the cells refed with fresh growth medium and then re-incubated in the carbon dioxide incubator to allow for cell growth. After 4–5 days of growth the culture plates were removed from the incubator and the cell culture medium was drained. The cells were detached from the plates with trypsin and counted in a Coulter Counter. For control cells or for cells treated with test compounds, cell growth was determined as a percentage of control. The concentration at which a given photoactivated test compound inhibited growth by 50% (the IC$_{50}$ in micromolar concentration, μM) was determined from the growth inhibition data. This value is shown in Table I for a variety of phototherapeutics.

TABLE I

Compound of Formula (5):

(8)

| R = | T = | photo-toxicity | dark-toxicity |
|---|---|---|---|
| H | HgCl | 6.1 | 15 |
| H | HgI | 1.3 | 4.2 |
| H | HgOAc | 4.8 | 6.2 |
| H | Hg-O-COCF$_3$ | 4.2 | 7.0 |
| F | HgOAc | 9.3 | 14 |
| CN | HgOAc | 20 | 30 |
| H | I | 1.1 | |
| H | N(CH$_2$CH$_2$OH)$_2$ | 0.31 | |
| H | pyridinium iodide salt | 0.37 | |
| H | morpholino | 3.2 | |
| H | dimethyl amino iodide salt | 0.1 | |
| H | 2,6-dimethylmorpholine | 0.01 | |
| Br | pyridinium iodide salt | 1.6 | |
| CN | pyridinium iodide salt | 1000 | |
| CN | Br | 6.4 | |
| CN | I | 2.1 | |
| Br | I | 0.48 | |
| I | I | 4.2 | |
| F | I | 62 | |
| Br | phthalimido | 3.9 | |
| F | Br | 4.0 | |
| H | H | 0.27 | |

TABLE I-continued

Compound of Formula (7):

| T = | Toxicity (IC$_{50}$ values in μM) | |
|---|---|---|
| | photo-toxicity | dark-toxicity |
| HgOAc | 6.1 | 11 |
| HgCl | 5.9 | 13 |
| HgI | 5.7 | 12 |

As shown by Table 1 mercury compounds demonstrated toxicity without light but no other compounds showed this dark toxicity effect. With light all mercury compounds demonstrated an enhanced toxicity.

Example 42

Fungicidal Assay

The antifungal activities of compounds synthesized were measured by determining the inhibition of growth of *Aspergillus niger* in a standard liquid medium. The liquid growth medium is described as a solution of mineral salts and yeast extract (MSY). The MSY broth was prepared as described in ASTM G21-70, and amended with glucose (10 g/l) and yeast extract (1 g/l). An aliquot (250 ml) of sterile medium was dispensed into each test well of a standard 96 well microplate (Corning No. 430247). Stock solutions of test compounds were prepared by dissolving the materials in 9:1 (v/v) solutions of acetone:methanol. Appropriate volumes of stock solutions were added to the test wells in order to achieve the desired ppm levels. Each test well (plus controls) was then inoculated with 5 mL of a standardized suspension of *Aspergillus niger*. The cell suspension was prepared by suspending viable cells from a slant of potato dextrose agar into sterile, deionized water. The suspension was then adjusted to provide OD$_{686}$=0.28. This density contains approximately 2.5×10$^7$ CFU (colony forming units)/ml. The microplates were incubated in the dark for four days at 28° C. The optical density for each well at 686 nm was then recorded automatically using a SpectraMax 340 microplate reader (Molecular Devices Corp., Sunnyvale, Calif.). All wells were visually inspected in order to corroborate data from the instrument. Test wells with an OD≦0.05 were judged to exhibit complete inhibition of cellular growth.

The antifungal activity was measured as minimum inhibitory concentrations or MIC of the 5'-substituted-4',5'-dihydropsoralens. Significant inhibition was observed at less than 100 ppm against such fungi as *Aspergillis niger*.

To assay the activity of the 5'-substituted-4',5'-dihydropsoralens of the invention against Chlorella, the Allen method (A. A. Allen, 1986, Journal of Phycology, 4, 1–4) was employed. The 5'-substituted-4',5'-dihydropsoralens demonstrated significant activity against Chlorella with MIC's<100 ppm. The antimicrobial activity found with the mercurio psoralens does not require ultraviolet light. The minimum inhibitory concentration (MIC) of the compounds tested against the fungus *Aspergillus niger* using an MSY broth is shown in Table II.

TABLE II

| | MIC |
|---|---|
| Compounds of Formula (5): | |
| (8) | |
| R = H, T = HgCl | <8 |
| R = H, T = HgI | <8 |
| R = H, T = HgOAc | <8 |
| R = H, T = HgOCOCF$_3$ | 16 |
| Compounds of Formula (7): | |
| (7) | |
| T = HgCl | 24 |
| T = HgI | <8 |
| T = HgOAc | 16 |

Example 43
Algicidal Assay

Test tubes containing modified Allen's medium were treated with increasing dosages of the compound to be tested and inoculated with a suspension of algal cells. After fourteen days of incubation, algal growth was rated as positive or negative. The minimum inhibitory concentration (MIC) of the compound is the smallest dosage showing negative algal growth.

The apparatus required consisted of sterilized test tubes, 18–150 mm and an incubator, capable of a constant (±2° C.) temperature within 26 to 28° C. The following procedure was used:

(1) Stock solutions (g/200 g deionized water each) were generated with: K$_2$HPO$_4$, 1.50 g; MgSO$_4$, 7H$_2$O, 1.50 g; Na$_2$CO$_3$, 0.80 g; CaCl$_2$ 2H$_2$O, 0.50 g; Na$_2$SiO$_3$ 9H$_2$O, 1.16 g, and Citric acid, 1.20 g.

(2) PIV metal stock solution (g/1000 g deionized water) was generated by the addition of: Na$_2$EDTA, 0.750 g; FeCl$_3$ 6H$_2$O, 0,097 g; MnCl$_2$ 4H$_2$O, 0.041 g; ZnCl$_2$, 0.005 g; CoCl$_2$ 6H$_2$O, 0.002 g and Na$_2$MoO$_4$ 2H$_2$O, 0.004 g.

(3) The modified Allen's medium was prepared in a volumetric flask by the addition of 1.5 g NaNO$_3$, 5.0 mL stock solution K$_2$HPO$_4$, 5.0 mL stock solution MgSO$_4$—7H$_2$O, 5.0 mL Stock solution Na$_2$CO$_3$, 10.0 mL stock solution CaCl$_2$ 2H$_2$O, 10.0 mL stock solution Na$_2$SiO$_3$ 9H$_2$O, 1.0 mL stock solution Citric acid and 1.0 mL stock solution PIV metal with enough deionized water to make 1000 mL of medium (Allen, 1968). The pH was adjusted to 7.8 and 5 mL of medium is added to each test tube. The tubes were sterilized in the autoclave for 20 minutes at 15 psi at 121° C. The test tubes were allowed to cool to 45–50° C. before adding the test compound and the inoculurn to the medium.

(4) The inoculum was a cell suspension from a 14-day-old culture of *Chlorella vulgaris* (UTEX 26, University of Texas) that was grown in modified Allen's medium.

The concentration of the stock solution in water or acetone of the compound to be tested is dependent on the largest dose required to be tested. Dilutions of the stock solution were made so that 100 μL of the stock solution of the corresponiding dilution was added per test tube. 100 μL of the solvent was added to the control to prepare the stock solution.

The inoculation consists of the addition of 100 μL of inoculurn per test tube.

The incubation of the control test tube and the test tubes containing compound and inoculum occurred in an incubator set between 26 to 28° C., with the temperature not varying more than ±2° C. Light was provided by plant growth fluorescent tubes and the test tubes were allowed to stand in the incubator for 14 days.

Rating of the test tubes containing different dosages of the compound will be positive or negative. If the medium in the tubes shows green coloration (algal growth), particularly at the bottom a positive (contaminated) the rating is given. If the medium in the rubes remains colorless, a negative (not contaminated) rating is given. The control is always positive. The minimum inhibitory concentration (MIC) of the compound is determined to be the smallest dosage showing negative algal growth. Table II shows the minimum inhibitory concentration (MIC) for each compound against the algae *Chlorella vulgar* using a modified Allens medium.

TABLE III

| | MIC |
|---|---|
| Compound of Formula (5): | |
| (8) | |
| R = H, T = HgCl | 10 |
| R = H, T = HgI | 9 |
| R = H, T = HgOAc | 10 |
| R = H, T = HgOCOCF$_3$ | 10 |
| Compounds of Formula (7): | |
| (7) | |
| T = HgCl | 10 |
| T = HgI | 10 |
| T = HgOAc | 10 |

Example 44
Antituberculosis Assays

Compounds were screened in a primary in vitro assay by The National Institute of Allergy and infectious diseases against *Mycobacterium tuberculosis* H37Rv. The primary screen was run using a BACTEC 460 system. Compounds were solubilized in dimethylsulfoxide at 1 mg/mL and sterilized by passage through 0.22 μm PFTE filters. Fifty μL was added to 4 mL BACTEC 128 medium (Becton Dickinson) to achieve a final concentration of 12.5 μg/mL. Approximately 4×10$^5$ colony forming units of M. tuberculosis H37Rv ATCC 27294 were added and the cultures were incubated at 37° C. Starting on the second day of the incubation, the Growth Index (GI, 1 GI=0.0025 dpm 1CO$_2$) was determined daily until the controls (drug-free) achieved a GI of 999. The percent inhibition was calculated as 1−(test sample GI÷control GI)×100 (Collins, 1997). The results are shown in Table IV.

TABLE IV

| | Anti-tubercular Activity (% inhibition) |
|---|---|
| Compound of Formula (5): (8) | |
| R = F, T = I | 31 |
| R = Br, T = I | 25 |
| R = H, T = I | 24 |
| R = I, T = I | 17 |
| R = H, T = N(CH$_3$)$_2$ HI salt | 4 |
| Compound of Formula (7): | |
| T = HgI | 99 |

What is claimed is:

1. A 5'-substituted 4,8-dimethyl-4',5'-dihydropsoralen of formula (5):

(5)

wherein
R is hydrogen, a halogen, NO$_2$, or CN; T is a halogen, or a group defined by NR$^1$R$^2$, (N$^+$R$^1$R$^2$R$^3$)X$^-$, or HgR$^4$; R$^1$ and R$^2$ are independently a C$_1$–C$_6$ alkyl, or R$^1$ and R$^2$ together with the nitrogen form a 5–8 member heterocyclic ring, or when T is a group defined by (N$^+$R$^1$R$^2$R$^3$)X$^-$, R$^1$ and R$^2$ together with the nitrogen form a 5–8 member heterocyclic ring or heterocyclic aromatic ring;
R$^3$ is hydrogen, a C$_1$–C$_{12}$ alkyl, or, when R$^1$ and R$^2$ together with the nitrogen form a heterocyclic aromatic ring, R$^3$ is a double bond within the heterocyclic aromatic ring;
X$^-$ is a halide;
R$^4$ is OC(O)(C$_1$–C$_6$ alkyl), OC(O)(C$_1$–C$_6$ fluoroalkyl), or a halogen; or a pharmaceutically acceptable salt thereof, with the proviso that when T is halogen or NR$^1$R$^2$, R is CN and when T is (N$^+$R$^1$R$^2$R$^3$)X$^-$, R is CN or NO$_2$.

2. A 5'-substituted 4,8-dimethyl-4',5'-dihydropsoralen of claim 1, wherein
R is hydrogen, F, Br, I, NO$_2$, or CN;
T is Br, I, or a group defined by NR$^1$R$^2$, (N$^+$R$^1$R$^2$R$^3$)X$^-$, or HgR$^4$;
R$^1$ and R$^2$ are independently methyl, ethyl, hydroxyethyl, or propyl, or R$^1$ and R$^2$ together with the nitrogen form a heterocyclic ring selected from N-pyrrolidinyl, N-2-pyrrolidinonyl, N-pyrrolinyl, N-pyrazolidinyl, N-pyrazolinyl, N-pyrazolyl, N-imidazolidinyl, N-imidazolinyl, N-imidazolyl, N-oxazolidinonyl, N-piperidinyl, N-piperazinyl, N-morpholinyl, N-pyridinyl, N-4-(C$_1$–C$_4$ alkyl)pyridinyl, N-hexamethyleneiminyl, N-heptamethyleneiminyl, N-quinolinyl or N-isoquinolyl;
R$^3$ is hydrogen, methyl, ethyl, dodecyl, or a double bond within a heterocyclic aromatic ring defined by N, R$^1$, and R$^2$;
X$^-$ is a bromide or iodide;
R$^4$ is OC(O)CH$_3$, OC(O)CF$_3$, Cl, Br, or I.

3. A 5'-substituted 4,8-dimethyl-4',5'-dihydropsoralen of claim 1, wherein
R is hydrogen, F, Br, I, NO$_2$, or CN;
T is Br, I, or a group defined by NR$^1$R$^2$, (N$^+$R$^1$R$^2$R$^3$)X$^-$, or HgR$^4$;
R$^1$ and R$^2$ are independently methyl, 2-hydroxyethyl, or propyl, or R$^1$ and R$^2$ together with the nitrogen form a heterocyclic ring selected from N-morpholinyl, N-pyridinyl, N-4-ethylpyridinyl, or N-quinolinyl;
R$^3$ is hydrogen, methyl, dodecyl, or a double bond within a heterocyclic aromatic ring defined by N, R$^1$, and R$^2$;
X$^-$ is a bromide or iodide;
R$^4$ is OC(O)CH$_3$, OC(O)CF$_3$, Cl, Br, or I.

4. A 5'-substituted 4,8-dimethyl-4',5'-dihydropsoralen of claim 1, wherein
T is a group defined by NR$^1$R$^2$, (N$^+$R$^1$R$^2$R$^3$)X$^-$, or HgR$^4$; when T is a group defined by NR$^1$R$^2$, R$^1$ and R$^2$ together with the nitrogen form a 5–8 member heterocyclic ring, or when T is a group defined by (N$^+$R$^1$R$^2$R$^3$)X$^-$, R$^1$ and R$^2$ together with the nitrogen form a 5–8 member heterocyclic ring or heterocyclic aromatic ring;
R$^3$ is hydrogen, a C$_1$–C$_{12}$ alkyl, or, when R$^1$ and R$^2$ together with the nitrogen form a heterocyclic aromatic ring, R$^3$ is a double bond within the heterocyclic aromatic ring.

5. A 5'-substituted 4,8-dimethyl-4',5'-dihydropsoralen of claim 1, selected from
3-Nitro-4,8-dimethyl-5'-(N-pyridiniummethyl)-4',5'-dihydropsoralen, bromide salt;
3-Nitro-4,8-dimethyl-5'-(N-4-ethylpyridiniummethlyl)-4',5'-dihydropsoralen bromide salt;
3-Nitro-4,8-dimethyl-5'-(N-quinoliniummethyl)-4',5'-dihydropsoralen, bromide salt;
3-Nitro-4,8-dimethyl-5'-(N,N,N-trimethylammonium methyl)-4',5'-dihydropsoralen bromide salt;
3-Cyano-4,8-dimethyl-5'-(bromomethyl)-4',5'-dihydropsoralen;
3-Cyano-4,8-dimethyl-5'-(iodomethyl)-4',5'-dihydropsoralen;
3-Cyano-4,8-dimethyl-5'-(N-pyridiniummethyl)-4',5'-dihydropsoralen, bromide salt;
3-Cyano-4,8-dimethyl-5'-(N-pyridiniummethyl)-4',5'-dihydropsoralen, iodide salt;

3-Cyano-4,8-dimethyl-5'-(N-4-ethylpyridiniummethyl)-4',5'-dihydropsoraicn bromide salt;

3-Cyano-4,8-dimethyl-5'-(N,N,N-trimethylammoniummethyl)-4',5'-dihydropsoralen bromide salt;

3-Cyano-4,8-dimethyl-5'-(N,N,N-trimethylammoniummethyl)-4',5'-dihydropsoralen iodide salt;

3-Fluoro-4,8-dimethyl-5'-acetomercurimethyl-4',5'-dihydropsoralen;

3-Iodo-4,8-dimethyl-5'-acetomercurimethyl-4',5'-dihydropsoralen;

4,8-Dimethyl-5'-acetomercurimethyl-4',5'-dihydropsoralen;

4,8-Dimethyl-5'-trifluoroacctomercurimethyl-4',5'-dlhydropsoralen;

4,8-Dimethyl-5'-chloromercurimethyl-4',5'-dihydropsoralen;

4,8-Dimethyl-5'-iodomercurimethyl-4',5'-dihydropsoralen;

3-Cyano-4,8-dimethyl-5'-acetomercurimethyl-4',5'-dihydropsoralen;

3-Fluoro-4,8-dimethyl-5'-acetomercurimethyl-4',5'-dihydropsoralen;

or a pharmaceutically acceptable salt thereof.

6. A process for preparing a 5'-substituted-4',5'-dihydropsoralen substituted at the 3, 4, 5, 8, or 4' position of formula (8):

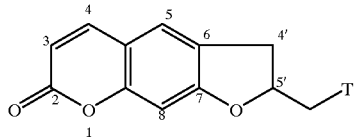

(8)

wherein T is Br or I, or $HgR^4$ wherein $R^4$ is $OC(O)(C_1-C_6$ alkyl), $OC(O)(C_1-C_6$ fluoroalkyl), or a halogen;

the process comprising the step of contacting a 6-allyl-7-hydroxycoumarin substituted at the 3, 4, 5, or 8 position of the formula:

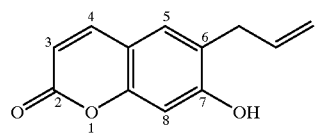

with a cyclization reagent under conditions to form said 5'-substituted-4',5'-dihydropsoralen substituted at the 3, 4, 5, 8, or 4' position;
when T is Br, the cyclization reagent is selected from N-bromosuccinimide;
when T is I, the cyclization reagent is selected from N-iodosuccinimide, $I_2$, ICl, and IBr; or
when T is $HgR^4$, the cyclization reagent is $Hg(R^4)_2$ wherein $R^4$ is as defined above.

7. A process for preparing a 5'-substituted 4,8-dimethyl-4',5'-dihydropsoralen of formula (5):

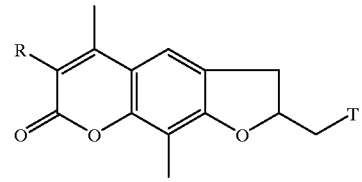

(5)

wherein R is hydrogen, a halogen, $NO_2$, or CN and T is BR or I, or $HgR^4$ wherein $R^4$ is $OC(O)(C_1-C_6$ alkyl), $OC(O)(C_1-C_6$ fluoroalkyl), or a halogen;

comprising the step of contacting a 4,8-dimethyl-6-allyl-7-hydroxycoumarin of the formula:

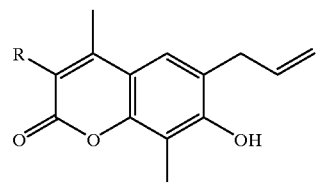

with a cyclization reagent under conditions to form said 5'-substituted 4,8-dimethyl-4',5'-dihydropsoralen, wherein:

R is as defined above; and when T is Br, the cyclization reagent is selected from N-bromosuccinimide;

when T is I, the cyclization reagent is selected from N-iodosuccinimide, $I_2$, ICl, and IBr; or when T is $HgR^4$, where $R^4$ is $R^4$ is $OC(O)(C_1-C_6$ alkyl), $OC(O)(C_1-C_6$ fluoroalkyl), or a halogen, the cyclization reagent is $Hg(R^4)_2$.

8. A process for preparing a 5'-substituted 4,8-dimethyl-4',5'-dihydropsoralen of claim 7, wherein R is hydrogen, F, Br, I, $NO_2$, or CN;

T is Br, I, or $HgR^4$; and $R^4$ is $OC(O)CH_3$, $OC(O)CF_3$, Cl, Br, or I.

9. A process for preparing a 3-R-4,8-dimethyl-4',5'-dihydro-5'-bromomethylpsoralen (5) having the formula:

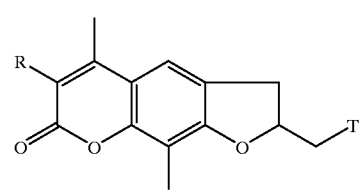

(5)

wherein R is hydrogen, a halogen, $NO_2$, or CN; and T is Br; comprising the steps of brominating a compound of formula (3)

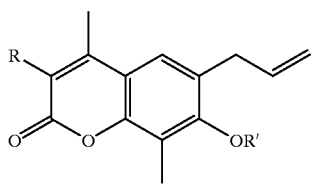
(3)

where R' is acetyl to form 4,8-dimethyl-6-(2,3-dibromopropyl)-7-acetoxycoumarin (4)

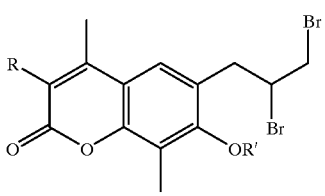
(4)

and cyclizing the resulting 3-R-4,8-dimethyl-6-(2,3-dibromopropyl)-7-hydroxycoumarin to yield the compound (5), wherein the cyclizing step comprises contacting the 3-R-4,8-dimethyl-6-(2,3-dibromopropyl)-7-hydroxycoumarin with anhydrous $K_2CO_3$ in dry acetone.

10. A process for preparing a 3-R-4,8-dimethyl-4',5'-dihydro-5'-bromomethylpsoralen of claim 9, wherein
R is hydrogen, F, Br, I, $NO_2$, or CN;
T is Br, I, or $HgR^4$; and
$R^4$ is $OC(O)CH_3$, $OC(O)CF_3$, Cl, Br, or I.

11. A process for preparing a 3-R-4,8-dimethyl-4',5'-dihydro-5'-iodomercurimethylpsoralen (5) having the formula:

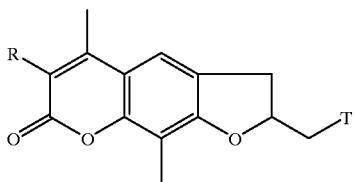
(5)

wherein R is hydrogen, a halogen, $NO_2$, or CN; and T is HgI; comprising the steps of:
contacting a 4,8-dimethyl-6-allyl-7-hydroxycoumarin of the formula:

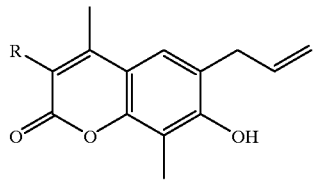

with a cyclization reagent under conditions to form said 3-R-4,8-dimethyl-4',5'-dihydro-5'-iodomercurimethylpsoralen, wherein:
R is hydrogen, a halogen, $NO_2$, or CN;
T is $HgR^4$;

$R^4$ is $OC(O)(C_1-C_6$ alkyl), $OC(O)(C_1-C_6$ fluoroalkyl), or a halogen, and the cyclization reagent is $Hg(R^4)_2$ and
contacting the resulting 3-R-4,8-dimethyl-4',5'-dihydro-5'-$R^4$mercurimethylpsoralen of formula (5) with $I^-$ under anion exchange conditions to convert the group $HgR^4$ to HgI.

12. A process for preparing 5-N-aminomethyl substituted 4,8-dimethyl-4',5'-dihydropsoralen of the formula (5):

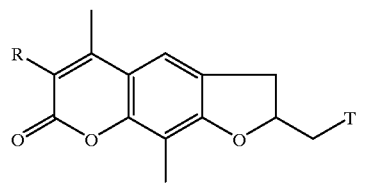
(5)

wherein
R is hydrogen, a halogen, $NO_2$, or CN;
T is $NR^1R^2$ or $(N^+R^1R^2R^3)X^-$;
$R^1$ and $R^2$ are independently a $C_1-C_6$ alkyl, or $R^1$ and $R^2$ together with the nitrogen form a 5–8 member heterocyclic ring, or when T is $(N^+R^1R^2R^3)X^-$, $R^1$ and $R^2$ together with the nitrogen form a 5–8 member heterocyclic ring or a 6-member heterocyclic aromatic ring;
$R^3$ is hydrogen, a $C_1-C_{12}$ alkyl, or, when $R^1$ and $R^2$ together with the nitrogen form a heterocyclic aromatic ring, $R^3$ is a double bond within the heterocyclic aromatic ring;
$X^-$ is bromo or iodo;
comprising the steps of:
contacting a 4,8-dimethyl-6-allyl-7-hydroxycoumarin of the formula:

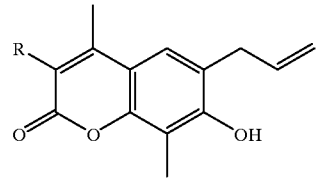

with a cyclization reagent under conditions to form a compound of formula (5) where T is Br or I, and wherein:
when T is Br, the cyclization reagent is selected from N-bromosuccinimide;
when T is I, the cyclization reagent is selected from N-iodosuccinimide, $I_2$, ICl, and IBr;
and contacting the compound of formula (5) where T is Br or I with an amine of the formula of $HNR^1R^2$ or $NR^1R^2R^3$.

13. A process for preparing 5-N-aminomethyl substituted 4,8-dimethyl-4',5'-dihydropsoralen of claim 12, wherein
R is hydrogen, F, Br, I, $NO_2$, or CN;
$R^1$ and $R^2$ are independently methyl, ethyl, hydroxyethyl, or propyl, or $R^1$ and $R^2$ together with the nitrogen form a heterocyclic ring selected from N-pyrrolidinyl, N-2-pyrrolidinonyl, N-pyrrolinyl, N-pyrazolidinyl, N-pyrazolinyl, N-pyrazolyl, N-imidazolidinyl, N-imidazolinyl, N-imidazolyl, N-oxazolidinonyl, N-piperidinyl, N-piperazinyl, N-morpholinyl, N-pyridinyl, N-4-($C_1-C_4$ alkyl)pyridinyl, N-hexamethylenciminyl, N-heptamethyleneiminyl, N-quinolinyl or N-isoquinolyl; and $R^3$ is hydrogen, methyl, ethyl, dodecyl, or a double bond within a heterocyclic aromatic ring defined by N, $R^1$, and $R^2$.

14. A process for preparing 5-N-aminomethyl substituted 4,8-dimethyl-4',5'-dihydropsoralen of claim 11, wherein R is hydrogen, F, Br, I, $NO_2$, or CN; and $R^1$ and $R^2$ are independently methyl, 2-hydroxyethyl, or propyl, or $R^1$ and $R^2$ together with the nitrogen form a heterocyclic ring selected from N-morpholinyl, N-pyridinyl, N-4-ethylpyridinyl, or N-quinolinyl; and $R^3$ is hydrogen, methyl, dodecyl, or a double bond within a heterocyclic aromatic ring defined by N, $R^1$, and $R^2$.

15. A process for preparing 5-N-aminomethyl substituted 4,8-dimethyl-4',5'-dihydropsoralen of the formula (5):

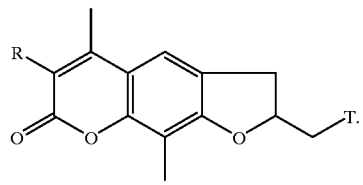

(5)

wherein

R is hydrogen, a halogen, $NO_2$, or CN;

T is $NR^1R^2$ or $(N^+R^1R^2R^3)X^-$;

$R^1$ and $R^2$ are independently a $C_1$–$C_6$ alkyl, or $R^1$ and $R^2$ together with the nitrogen form a 5–8 member heterocyclic ring, or when T is $(N^+R^1R^2R^3)X^-$, $R^1$ and $R^2$ together with the nitrogen form a 5–8 member heterocyclic ring or a 6-member heterocyclic aromatic ring;

$R^3$ is hydrogen, a $C_1$–$C_{12}$ alkyl, or, when $R^1$ and $R^2$ together with the nitrogen form a heterocyclic aromatic ring, $R^3$ is a double bond within the heterocyclic aromatic ring;

$X^-$ is bromo or iodo;

comprising the steps of:

brominating a compound of formula (3)

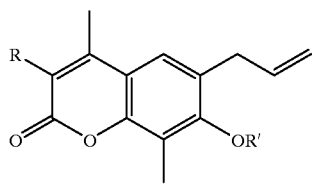

(3)

where R' is acetyl to form 4,8-dimethyl-6-(2,3-dibromopropyl)-7-acetoxycoumarin (4)

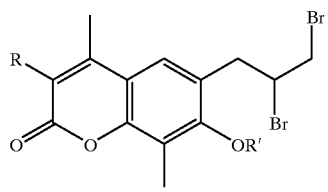

(4)

and cyclizing the resulting 3-R-4,8-dimethyl-6-(2,3-dibromopropyl)-7-hydroxycoumarin to yield the compound (5); and contacting the compound of formula (5) where T is Br or I with an amine of the formula of $HNR^1R^2$ or $NR^1R^2R^3$, wherein the cyclizing step comprises contacting the 3-R-4,8-dimethyl-6-(2,3-dibromopropyl)-7-hydroxycoumarin with anhydrous $K_2CO_3$ in dry acetone.

16. A process for preparing 5-N-aminomethyl substituted 4,8-dimethyl-4',5'-dihydropsoralen of claim 16, wherein R is hydrogen, F, Br, I, $NO_2$, or CN;

$R^1$ and $R^2$ are independently methyl, ethyl, hydroxyethyl, or propyl, or $R^1$ and $R^2$ together with the nitrogen form a heterocyclic ring selected from N-pyrrolidinyl, N-2-pyrrolidinonyl, N-pyrrolinyl, N-pyrazolidinyl, N-pyrazolinyl, N-pyrazolyl, N-imidazolidinyl, N-imidazolinyl, N-imidazolyl, N-oxazolidinonyl, N-piperidinyl, N-piperazinyl, N-morpholinyl, N-pyridinyl, N-4-($C_1$–$C_4$ alkyl)pyridinyl, N-hexamethyleneiminyl, N-heptamethyleneiminyl, N-quinolinyl or N-isoquinolyl; and $R^3$ is hydrogen, methyl, ethyl, dodecyl, or a double bond within a heterocyclic aromatic ring defined by N, $R^1$, and $R^2$.

17. A process for preparing 5-N-aminomethyl substituted 4,8-dimethyl-4',5'-dihydropsoralen of claim 15, wherein R is hydrogen, F, Br, I, $NO_2$, or CN; and $R^1$ and $R^2$ are independently methyl, 2-hydroxyethyl, or propyl, or $R^1$ and $R^2$ together with the nitrogen form a heterocyclic ring selected from N-morpholinyl, N-pyridinyl, N-4-ethylpyridinyl, or N-quinolinyl; and $R^3$ is hydrogen, methyl, dodecyl, or a double bond within a heterocyclic aromatic ring defined by N, $R^1$, and $R^2$.

18. A process for preparing 5-N-aminomethyl substituted 4,8-dimethyl-4',5'-dihydropsoralen of claim 15, wherein the cyclization step yields a mixture of 3-R-4,8-dimethyl-4',5'-dihydro-5'-bromomethylpsoralen (5) and a compound (6)

(6)

and the resulting mixture is contacted with an amine of the formula of $HNR^1R^2$ or $NR^1R^2R^3$ without separation.

19. A method for treating a proliferative skin disorder in a mammal comprising administering to the mammal an effective amount of a compound according to claim 1 and then irradiating the mammal with ultraviolet light.

20. A method according to claim 19, wherein the compound is administered, topically, parenterally, or orally.

21. A method for treating a proliferative skin disorder in a mammal comprising administering to the mammal an effective amount of a compound according to claim 1 where T is $HgR^4$.

22. A method according to claim 21, wherein the compound is administered, topically, parenterally, or orally.

23. A pharmaceutical composition comprising a therapeutically effective amount of a compound according to claim 1 and a pharmaceutically acceptable carrier.

24. A 5'-substituted 4,8-dimethyl-4',5'-dihydropsoralen of claim 1 wherein T is $HgR^4$.

25. A pharmaceutical composition comprising a therapeutically effective compound according to claim 24 and a pharmaceutically acceptable carrier.

* * * * *